(12) United States Patent
Block et al.

(10) Patent No.: US 12,337,026 B2
(45) Date of Patent: Jun. 24, 2025

(54) METHODS OF TREATING INFLAMMATORY DISORDERS WITH MULTIVALENT FC COMPOUNDS

(71) Applicant: Gliknik Inc., Baltimore, MD (US)

(72) Inventors: David S. Block, Baltimore, MD (US); Henrik Olsen, Baltimore, MD (US)

(73) Assignee: Gliknik Inc., Baltimore, MD (US)

(*) Notice: Subject to any disclaimer, the term of this patent is extended or adjusted under 35 U.S.C. 154(b) by 531 days.

(21) Appl. No.: 17/718,822

(22) Filed: Apr. 12, 2022

(65) Prior Publication Data

US 2022/0241372 A1 Aug. 4, 2022

Related U.S. Application Data

(62) Division of application No. 16/467,859, filed as application No. PCT/US2017/065400 on Dec. 8, 2017, now Pat. No. 11,331,372.

(60) Provisional application No. 62/432,407, filed on Dec. 9, 2016.

(51) Int. Cl.
C07K 16/36 (2006.01)
A61K 38/17 (2006.01)
G01N 33/53 (2006.01)

(52) U.S. Cl.
CPC .................. *A61K 38/1709* (2013.01)

(58) Field of Classification Search
CPC ............ A61K 38/1709; C07K 2317/52; C07K 16/36; G01N 33/53; G01N 2800/52
USPC ...................................................... 424/133.1
See application file for complete search history.

(56) References Cited

U.S. PATENT DOCUMENTS

| | | | |
|---|---|---|---|
| 5,681,566 A | 10/1997 | Stevenson | |
| 5,877,396 A | 3/1999 | Ravetch et al. | |
| 6,004,781 A | 12/1999 | Seed | |
| 6,660,266 B1 | 12/2003 | Mosser et al. | |
| 6,737,056 B1 | 5/2004 | Presta | |
| 7,148,321 B2 | 12/2006 | Gillies et al. | |
| 7,511,121 B2 | 3/2009 | Arnason et al. | |
| 7,524,487 B2 | 4/2009 | Mosser et al. | |
| 7,666,622 B2 | 2/2010 | Sharma et al. | |
| 8,258,263 B2 | 9/2012 | Morrison et al. | |
| 8,680,237 B2 | 3/2014 | Strome et al. | |
| 9,164,088 B2 | 10/2015 | Olson et al. | |
| 9,512,208 B2 | 12/2016 | Strome et al. | |
| 9,512,210 B2 | 12/2016 | Strome et al. | |
| 9,683,044 B2 | 6/2017 | Block et al. | |
| 9,926,362 B2 | 3/2018 | Strome et al. | |
| 10,208,105 B2 | 2/2019 | Strome et al. | |
| 10,851,154 B2 | 12/2020 | Strome et al. | |
| 10,941,191 B2 | 3/2021 | Strome et al. | |
| 11,034,775 B2 | 6/2021 | Olsen et al. | |
| 11,117,940 B2 | 9/2021 | Block et al. | |
| 11,331,372 B2 | 5/2022 | Block et al. | |
| 2002/0115157 A1 | 8/2002 | Davis et al. | |
| 2002/0142374 A1 | 10/2002 | Gallo et al. | |
| 2002/0147326 A1 | 10/2002 | Chaikin et al. | |
| 2003/0044423 A1 | 3/2003 | Gillies et al. | |
| 2003/0118592 A1 | 6/2003 | Ledbetter et al. | |
| 2003/0216546 A1 | 11/2003 | Tykocinski et al. | |
| 2003/0235578 A1 | 12/2003 | Stinson et al. | |
| 2004/0062763 A1 | 4/2004 | Mosser et al. | |
| 2004/0110226 A1 | 6/2004 | Lazar et al. | |
| 2004/0147731 A1 | 7/2004 | Parkos | |
| 2004/0151725 A1 | 8/2004 | Gray et al. | |
| 2004/0265321 A1 | 12/2004 | Johnson et al. | |
| 2005/0033029 A1 | 2/2005 | Lu | |
| 2005/0042602 A1 | 2/2005 | Ahearn et al. | |
| 2005/0249723 A1 | 11/2005 | Lazar | |
| 2006/0074225 A1 | 4/2006 | Chamberlain et al. | |
| 2006/0263856 A1 | 11/2006 | Gillies et al. | |
| 2006/0275254 A1 | 12/2006 | Kim et al. | |
| 2007/0269369 A1 | 11/2007 | Gegg et al. | |
| 2008/0260738 A1 | 10/2008 | Moore et al. | |
| 2008/0267980 A1 | 10/2008 | Tomlinson et al. | |
| 2009/0104210 A1 | 4/2009 | Tota et al. | |
| 2009/0117133 A1 | 5/2009 | Arnason et al. | |
| 2009/0136485 A1 | 5/2009 | Chu et al. | |

(Continued)

FOREIGN PATENT DOCUMENTS

AU 2015200330 B2 10/2016
CN 101835802 A 9/2010

(Continued)

OTHER PUBLICATIONS

Abaza, et al., "Effect of amino acid substitutions outside an antigenic site on protein binding to monoclonal antibodies of predetermined specificity obtained by peptide immunization: demonstration with region 94-100 (antigenic site 3) of myoglobin." Journal of Protein Chemistry (1992); 11 (5): 433-444.

Anderson, C. A. et al., "Cutting Edge: Biasing immune responses by directing antigen to macrophage Fcγ receptors." J. Immunology (2002); 168: 3697-3701.

(Continued)

*Primary Examiner* — Yan Xiao
(74) *Attorney, Agent, or Firm* — COOLEY LLP

(57) ABSTRACT

The present invention provides methods for the identification of patients with an inflammatory or autoimmune disease that demonstrate an inadequate response to treatment with a multi-Fc therapeutic, and the determination of an optimal dose of a multi-Fc therapeutic for said patient based on the patient's circulating levels of inactivated C3b (iC3b) and/or additional complement components that may be employed as a surrogate for iC3b based on an analogous response to multi-Fc therapeutics. The present invention further provides for improvements in the use of such multi-Fc therapeutics in the treatment of autoimmune and inflammatory diseases.

20 Claims, 9 Drawing Sheets

Specification includes a Sequence Listing.

(56) References Cited

U.S. PATENT DOCUMENTS

| | | |
|---|---|---|
| 2009/0175867 A1 | 7/2009 | Thompson et al. |
| 2009/0217401 A1 | 8/2009 | Korman et al. |
| 2009/0252729 A1 | 10/2009 | Farrington et al. |
| 2009/0258031 A1 | 10/2009 | Karrer et al. |
| 2009/0304696 A1 | 12/2009 | Lawson et al. |
| 2009/0304715 A1 | 12/2009 | Masuho et al. |
| 2010/0048877 A1 | 2/2010 | Ruker et al. |
| 2010/0093979 A1 | 4/2010 | Lazar |
| 2010/0135987 A1 | 6/2010 | Hickman et al. |
| 2010/0143353 A1 | 6/2010 | Mosser et al. |
| 2010/0227805 A1 | 9/2010 | Karin et al. |
| 2010/0239633 A1 | 9/2010 | Strome et al. |
| 2011/0243966 A1 | 10/2011 | Farrington et al. |
| 2011/0305697 A1 | 12/2011 | Walczak |
| 2012/0100140 A1 | 4/2012 | Reyes et al. |
| 2012/0283417 A1 | 11/2012 | Mosser et al. |
| 2012/0309941 A1 | 12/2012 | Strome et al. |
| 2012/0315266 A1 | 12/2012 | Olson et al. |
| 2013/0156765 A1 | 6/2013 | Block et al. |
| 2014/0072582 A1 | 3/2014 | Block et al. |
| 2014/0105913 A1 | 4/2014 | Strome et al. |
| 2014/0335075 A1 | 11/2014 | Strome et al. |
| 2014/0370012 A1 | 12/2014 | Block et al. |
| 2015/0056185 A1 | 2/2015 | Strome et al. |
| 2015/0152406 A1 | 6/2015 | Grawunder |
| 2015/0218236 A1 | 8/2015 | Pleass |
| 2015/0301058 A1 | 10/2015 | Schettini et al. |
| 2016/0229913 A1 | 8/2016 | Bosques et al. |
| 2016/0280768 A1 | 9/2016 | Strome et al. |
| 2016/0355570 A1 | 12/2016 | Strome et al. |
| 2017/0008951 A1 | 1/2017 | Block et al. |
| 2017/0029505 A1 | 2/2017 | Griffin et al. |
| 2017/0081406 A1 | 3/2017 | Fallah-Arani et al. |
| 2017/0088603 A1 | 3/2017 | Fallah-Arani et al. |
| 2018/0002388 A1 | 1/2018 | Block et al. |
| 2018/0094061 A1 | 4/2018 | Block et al. |
| 2018/0186862 A1 | 7/2018 | Strome et al. |
| 2019/0218275 A1 | 7/2019 | Strome et al. |
| 2020/0069769 A1 | 3/2020 | Block et al. |
| 2021/0277091 A1 | 9/2021 | Strome et al. |
| 2022/0056087 A1 | 2/2022 | Block et al. |

FOREIGN PATENT DOCUMENTS

| | | |
|---|---|---|
| CN | 103249432 A | 8/2013 |
| EP | 0553667 A1 | 8/1993 |
| EP | 0439540 B1 | 6/1995 |
| EP | 2006305 A9 | 7/2009 |
| JP | 2015518570 A | 7/2015 |
| WO | WO-9004413 A1 | 5/1990 |
| WO | WO-9403191 A1 | 2/1994 |
| WO | WO-9415640 A1 | 7/1994 |
| WO | WO-0009560 A2 | 2/2000 |
| WO | WO-02056910 A1 | 7/2002 |
| WO | WO-02072605 A2 | 9/2002 |
| WO | WO-02072608 A2 | 9/2002 |
| WO | WO-03010202 A1 | 2/2003 |
| WO | WO-03051933 A1 | 6/2003 |
| WO | WO-03105898 A1 | 12/2003 |
| WO | WO-2004062619 A2 | 7/2004 |
| WO | WO-2005000895 A2 | 1/2005 |
| WO | WO-2005007809 A2 | 1/2005 |
| WO | WO-2005077981 A2 | 8/2005 |
| WO | WO-2005089503 A2 | 9/2005 |
| WO | WO-2006008739 A2 | 1/2006 |
| WO | WO-2006061650 A2 | 6/2006 |
| WO | WO-2006071206 A2 | 7/2006 |
| WO | WO-2006074199 A1 | 7/2006 |
| WO | WO-2007021129 A1 | 2/2007 |
| WO | WO-2007100083 A1 | 9/2007 |
| WO | WO-2008138131 A1 | 11/2008 |
| WO | WO-2008151088 A2 | 12/2008 |
| WO | WO-2008157378 A2 | 12/2008 |
| WO | WO-2010065578 A2 | 6/2010 |
| WO | WO-2010094722 A2 | 8/2010 |
| WO | WO-2011060242 A2 | 5/2011 |
| WO | WO-2011073692 A1 | 6/2011 |
| WO | WO-2011163412 A1 | 12/2011 |
| WO | WO-2012001647 A2 | 1/2012 |
| WO | WO-2012016073 A2 | 2/2012 |
| WO | WO-2013112986 A1 | 8/2013 |
| WO | WO-2013166030 A2 | 11/2013 |
| WO | WO-2014031646 A2 | 2/2014 |
| WO | WO-2014143185 A1 | 9/2014 |
| WO | WO-2015017822 A1 | 2/2015 |
| WO | WO-2015070041 A1 | 5/2015 |
| WO | WO-2015132364 A1 | 9/2015 |
| WO | WO-2015132365 A1 | 9/2015 |
| WO | WO-2015158867 A1 | 10/2015 |
| WO | WO-2015168643 A2 | 11/2015 |
| WO | WO-2016009232 A1 | 1/2016 |
| WO | WO-2016073917 A1 | 5/2016 |
| WO | WO-2016139365 A1 | 9/2016 |
| WO | WO-2016179472 A2 | 11/2016 |
| WO | WO-2017005767 A1 | 1/2017 |
| WO | WO-2017013203 A1 | 1/2017 |
| WO | WO-2017019565 A2 | 2/2017 |
| WO | WO-2017036905 A1 | 3/2017 |
| WO | WO-2017151971 A2 | 9/2017 |
| WO | WO-2017176651 A1 | 10/2017 |
| WO | WO-2017214321 A1 | 12/2017 |
| WO | WO-2018018047 A2 | 1/2018 |
| WO | WO-2018107079 A1 | 6/2018 |
| WO | WO-2018107082 A1 | 6/2018 |

OTHER PUBLICATIONS

Arase, et al., "Association with FcRγ is Essential for Activation Signal through NKR-P1 (CD161) in Natural Killer (NK) Cells and NK1.1+ T Cells." Journal of Experimental Medicine (1997); 186 (12): 1957-1963.

Asanuma, et al., "Multimerization and collagen binding of vitronectin is modulated by its glycosylation." International Congress Series (2001); vol. 1223, pp. 97-101.

Aubin, et al., "Indirect inhibition of in vivo and in vitro T-cell responses by intravenous immunoglobulins due to impaired antigen presentation." Blood (2010); 115 (9): 1727-1734.

Banki, et al., "Cross-Linking of CD32 Induces Maturation of Human Monocyte-Derived Dendritic Cells Via NF-B Signaling Pathway." The Journal of Immunology (2003); 170 (8): 3963-3970.

Bleeker, et al., "Vasoactive side effects of intravenous immuno-globulin preparations in a rat model and their treatment with recombinant platelet-activating factor acetylhydrolase". Blood (Mar. 1, 2000); 95(5): 1856-1861.

Brønsted, et al., "Crosslinked dextran—a new capsule material for colon targeting of drugs." Journal of Controlled Release (Apr. 30, 1998); 53(1-3): 7-13.

Bruhns, et al., "Specificity and affinity of human Fcγ receptors and their polymorphic variants for human IgG subclasses." Blood (2009); 113 (16): 3716-3725.

Campbell, A. M., "Monoclonal Antibody Technology," In Laboratory Techniques in Biochemistry and Molecular Biology (1984); vol. 13, Elsevier Science Publishers, pp. 1-32.

Chougnet, et al., "Molecular analysis of decreased interleukin-12 production in person infected with human immunodeficiency virus." J. Infectious Diseases (1996); 174: 46-53.

Cohen, P., "Systemic Autoimmunity," In Fundamental Immunology, 4th edition, Philadelphia, Lippencot-Raven Publishers, pp. 1067-1088 (1999).

Colman, P. M. "Effects of amino acid sequence changes on antibody-antigen interactions", Research in Immunology, (Jan. 1994); 145(1):33-36.

Constantine, M. M., et al., "Intravenous immunoglobulin utilization in the Canadian Atlantic provinces: a report of the Atlantic Collaborative Intravenous Immune Globulin utilization working group." Transfusion (2007); 47: 2072-2080.

Davidson, et al, "T helper cell1-type CD4+ T cells, but not B cells, mediate colitis in interleukin 10-deficient mice." J. Exp. Med. (1996); 184: 241-251.

(56) References Cited

OTHER PUBLICATIONS

Debré, et al., "Infusion of Fcγ fragments for treatment of children with acute immune thrombocytopenia purpura." Lancet (1993); 342: 945-949.
Deo, Y. M. et al., "Clinical significance of IgG Fc receptors and FcγR-directed immunotherapies." Immunology Today (1997); 18 (3):127-135.
Dinarello, C. A., "Proinflammatory and anti-inflammatory cytokines as mediators in the pathogenesis of septic shock." Chest (1997); 112: 321S-329S.
Extended European Search Report for EP Application No. 13169230.3, dated Oct. 25, 2013, 15 pages.
Gavin, et al., "Cutting Edge: Identification of the Mouse IgG3 Receptor: Implications for Antibody Effector Function at the Interface Between Innate and Adaptive Immunity." J. Immunol. (1998); 160 (1): 20-23.
Gerber, et al., "Reversing Lipopolysaccharide Toxicity by Ligating the Macrophage Fcγ Receptors." J. Immunology (2001); 166: 6861-6868.
Gralnick, et al., "Role of carbohydrate in multimeric structure of factor VIII/von Willebrand factor protein." PNAS (1983); 80 (9): 2771-2774.
Ha, et al., "Isolation and characterization of IgG1 with asymmetrical Fc glycosylation." Glycobiology (2011); 21 (8): 1087-1096.
Harbury, et al. "A switch between two-, three-, and four-stranded coiled coils in GCN4 leucine zipper mutants." Science (1993); 262: 1401-1407.
Hart, et al., "Comparison of the suppressive effects of interleukin-10 and interleukin-4 on synovial fluid macrophages and blood monocytes from patients with inflammatory arthritis." Immunology (1995); 84: 536-542.
Jain, et al., "Tumour antigen targeted monoclonal antibodies incorporating a novel multimerisation domain significantly enhance antibody dependent cellular cytotoxicity against colon cancer." European Journal of Cancer (2013); 49 (15): 3344-3352.
Jukes, et al., "A Newly Developed Chemically Crosslinked Dextran-Poly(Ethylene Glycol) Hydrogel for Cartilage Tissue Engineering." Tissue Engineering Part A (2010); 16(2): 565-573.
Lee, J. K. "Determination of the Molecular Size Distribution of Immunoglobulin G (IgG) in Intravenous IgG-Albumin Formulations by High-Performance Liquid Chromatography." Journal of Chromatography (1988); 444: 141-152.
Lemieux and Bazin, "Autoantibody-Induced Formation of Immune Complexes in Normal Human Serum." Curr. Pharm Design (2006); 12: 173-179.
Levinson, D. R., "Intravenous Immune Globulin: Medicare payment and availability." Report to DHHS, OEI-03-05-00404 (2007), 31 pages.
Liew, "TH1 and TH2 cells: a historical perspective." Nature Reviews, Immunology (2002);2: 55-60.
Lucas, et al., "ERK activation following macrophage FcγR ligation leads to chromatin modifications at the IL-10 locus." Journal of Immunology (2005); 175: 469-477.
Meijer, et al., "Pharmacokinetics of Murine Anti-Human CD3 Antibodies in Man Are Determined by the Disappearance of Target Antigen." Journal of Pharmacology and Experimental Therapeutics (2002); 300 (1): 346-353.
Mendel and Mendel, "'Non-specific' binding. The problem, and a solution." Biochemical Journal (1985); 228 (1): 269-272.
Monoclonal antibody 13-1 heavy chain-mouse, GenBank Accession # PC4436 (Date: Feb. 4, 1998), 2 pages.
Morris, et al., "Development and characterization of recombinant human Fc:OX40L fusion protein linked via a coiled-coil trimerization domain." Molecular Immunology (2007); 44 (12): 3112-3121.
Mosser, D. M., "The Many Faces of Macrophage Activation." J. Leukocyte Biology (2003); 73: 209-212.
Mosser, et al., "Interleukin-10: new perspectives on an old cytokine." Immunological Reviews (2008); 226 (1): 205-218.
Mössner, et al., "Increasing the efficacy of CD20 antibody therapy through the engineering of a new type II anti-CD20 antibody with enhanced direct and immune effector cell-mediated B-cell cytotoxicity." Blood (2010); 115 (22): 4393-4402.
Nagashima, et al., "Enhanced antibody-dependent cellular phagocytosis by chimeric monoclonal antibodies with tandemly repeated Fc domains." Journal of Bioscience and Bioengineering (2011); 111 (4): 391-396.
Nagashima, et al., "Fc Taryotaika ni yoru Kokassei Kotai." Proc. 126th Ann. Meet. Pharm. Soc. Japan 126:107 (abstract No. P28[S]am-551) (2006).
Nagashima, et al., "Tandemly repeated Fc domain augments binding avidities of antibodies for Fcγ receptors, resulting in enhanced antibody-dependent cellular cytotoxicity." Mol. Immunol. (2008); 45: 2752-2763.
Ngo, J.T., et al., "Computational Complexity, Protein Structure Prediction, and the Levinthal Paradox," The Protein Folding Problem and Tertiary Structure Prediction, Merz et al., (ed.), Birkhauser, Boston, MA, 1994, pp. 491-495.
Nimmerjahn and Ravetch, "Antibody-mediated modulation of immune responses." Immunological Rev. (2010); 236: 265-275.
Nimmerjahn and Ravetch, "The antiinflammatory activity of IgG: the intravenous IgG paradox." Journal of Experimental Medicine (2007); 204 (1): 11-15.
O'Shea, et al., "Evidence that the leucine zipper is a coiled coil." Science (1989); 243 (4890): 538-542.
Ratcliffe et al., "Measurement of the binding activity of defined IgG aggregates to macrophage Fc receptors," Immunology Letters, 7(2):73-76 (1983).
Reeth et al., "Positive selection vectors to generate fused genes for the expression of his-tagged proteins." BioTechniques (1998); 25: 898-904.
Rudikoff, S. et al. "Single amino acid substitution altering antigen-binding specificity", Proc Natl Acad Sci, (Mar. 1982); 79:1979-1983.
Shields, et al., "Lack of Fucose on Human IgG1 N-Linked Oligosaccharide Improves Binding to Human FcγRIII and Antibody-dependent Cellular Toxicity." The Journal of Biological Chemistry (2002); 277 (30): 26733-26740.
Siragam, et al., "Can antibodies with specificity for soluble antigens mimic the therapeutic effects of intravenous IgG in the treatment of autoimmune disease?" The Journal of Clinical Investigation (2005); 115 (1): 155-160.
Smith and Morrison, "Recombinant polymeric IgG: an approach to engineering more potent antibodies." Biotechnol. (1994); 12: 683-688.
Song, et al., "Monoclonal IgG can ameliorate immune thrombocytopenia in a murine model of ITP: an alternative to IVIG." Blood (2002); 101 (9): 3708-3713.
Stevenson, G. T. et al., "Engineered antibody for treating lymphoma." Recent Res. Canc. Res. (2002); 159: 104-112.
Sundaram, et al., "Lipopolysaccharide-induced suppression of erythrocyte binding and phagocytosis via FcγRI, FcγRII, FcγRIII, and CR3 receptors in murine macrophages." J. Leukocyte Biology (1993); 54: 81-88.
Sutterwala, et al., "Selective Suppression of Interleukin-12 Induction After Macrophage Receptor Litigation." J. Exp. Med. (1985); 185: 1977-1985.
Sutterwala, et al., "Reversal of Proinflammatory Responses by Ligating the macrophage Fcγ Receptor Type I." Journal of Experimental Medicine (1998); 188 (1): 217-222.
Tankersley, D. L., "Dimer Formation in immunoglobulin Preparations and Speculations on the Mechanism of Action of Intravenous Immune Globulin in Autoimmune Diseases." Immunological Reviews (1994); 39: 159-172.
Tha-In, et al., "Modulation of the cellular immune system by intravenous immunoglobulin." Trends Immunol. (2008); 29 (12): 608-615.
Tremblay, et al., "Picogram doses of lipopolysaccharide exacerbate antibody-mediated thrombocytopenia and reduce the therapeutic efficacy of intravenous immunoglobulins in mice." British Journal of Hematology (2007); 139: 297-302.

(56) References Cited

OTHER PUBLICATIONS

Vajdos F.F., et al., "Comprehensive Functional Maps of the Antigen-Binding Site of an Anti-ErbB2 Antibody Obtained with Shotgun Scanning Mutagenesis," Journal of Molecular Biology, Jul. 2002, vol. 320 (2), pp. 415-428.

Vialtel, et al., "Nucleation-controlled Polymerization of human Monoclonal Immunoglobulin G Cryoglobulins." The Journal of Biological Chemistry (1982); 257 (7): 3811-3818.

Weber, et al., "B-cell activation influences T-cell polarization and outcome of anti-CD20 B-cell depletion in central nervous system autoimmunity." Annals of Neurology (2010); 68 (3): 369-383.

Woof, et al., "Human antibody-Fc receptor interactions illuminated by crystal structures." Nat Rev Immunol. (Feb. 2004); 4(2): 89-99.

Wright and Morrison, "Effect of C2-Associated Carbohydrate Structure on Ig Effector Function: Studies with Chimeric Mouse-Human IgG1 Antibodies in Glycosylation Mutants of Chinese Hamster Ovary Cells." The Journal of Immunology (1998); 160 (7): 3393-3402.

Wright, et al., "Dimeric, Trimeric and Tetrameric Complexes of Immunoglobulin G Fix Complement." Biochem. J. (1980); 187: 775-780.

"Synthetic peptides with high biochemical activity," downloaded on Sep. 7, 2012 from http://www.genosphere-biotech.com/Long-Active-Peptides.html, 1 page.

Zafranskaya, et al., "Interferon-therapy reduces CD4+ and CD8+ T-cell reactivity in multiple sclerosis." Immunology (May 2007); 121(1): 29-39. Epub Dec. 18, 2006.

Zang, C., "Annual founders week deemed a 'huge success,'" VOICE University of Maryland, pp. 1-5, http://umvoice.com/2011/12/annual-founders-week-deemed-a-huge-success/, visited website Dec. 10, 2012.

Zhang, et al., "Alteration in the IL-2 signal peptide affects secretion of proteins in vitro and in vivo." Journal Gene Medicine (2005); 7: 354-365.

Zhang, et al., "Dynamic and transient remodeling of the macrophages IL-10 promoter during transcription." Journal of Immunology (2006); 177: 1282-1288.

Gelfand, E.W., "Intravenous immune globulin in autoimmune and inflammatory diseases". N Engl J Med. Nov. 22, 2012; 367(21): 2015-2025.

Lutz, H.U., et al., "Intravenously applied IgG stimulates complement attenuation in a complement-dependent autoimmune disease at the amplifying C3 convertase level," Blood. Jan. 15, 2004; 103(2): 465-472. Epub Sep. 25, 2003.

Schramm E.C., et al., "A Quantitative Lateral Flow Assay to Detect Complement Activation in Blood," Anal Biochem. May 15, 2015; 477: 78-85. Epub Feb. 4, 2015.

Ueda et al., "Identification of the complement iC3b binding site in the β2 integrin CR3 (CD11b/CD18)", Proc Natl Acad Sci U S A. Oct. 25, 1994; 91(22): 10680-10684.

Alegre and Fallarino, "Mechanisms of CTLA-4-Ig in tolerane induction." Curr. Pharmaceutical Design (2006); 12 (2): 149-160.

Amarilyo, et al., "iC3bopsonized apoptotic cells mediate a distinct anti-inflammatory response and transcriptional NF-kB-dependent blockade". European Journal of Immunology (Mar. 3, 2010); 40(3): 699-709.

Augener, et al., "Are aggregates of IgG the effective part of high-dose immunoglobulin therapy in adult idiopathic thrombocytopenia purpura (ITP)?" Blut (1985); 50: 249-252.

Baerenwaldt, et al., "Mechanisms of action of intravenous immunoglobulins." Expert Rev Clin Immunol. (May 2010); 6: 425-434.

Barrionuevo, et al., "Immune complex-FcR interaction modulates monocyte/macrophage molecules involved in inflammation and immune response." Clin. Exp. Immunol. (2003); 133 (2): 200-207.

Bazin, et al., "Reversal of immune thrombocytopenia in mice by cross-linking human immunoglobulin G with a high-affinity monoclonal antibody". Br J Haematol. (Oct. 2006); 135(1): 97-100. Epub Aug. 22, 2006.

Bazin, et al., "Tetramolecular immune complexes are more efficient than IVIg to prevent antibody-dependent in vitro and in vivo and in vivo phagocytosis of blood cells." British J. Haematol. (2004); 127 (1): 90-96.

Boyle, J.J., et al., "Solid-Phase Immunoglobulins IgG and IgM Activate Macrophages with Solid-Phase IgM Acting via a Novel Scavenger Receptor A Pathway." The American Journal of Pathology (2012); 181 (1): 347-361.

Braathen, R., et al., "The Carboxyl-terminal Domains of IgA and IgM Direct Isotype-specific Polymerization and Interaction with the Polymeric Immunoglobulin Receptor." The Journal of Biological Chemistry (2002); 277 (45): 42755-42762.

Caron, et al., "Engineered Humanized Dimeric Forms of IgG are More Effective Antibodies." J. Exp. Med. (1992); 176: 1191-1195.

Chappel, et al., "Identification of the Fc receptor class I binding site in human IgG through the use of recombinant IgG1/IgG2 hybrid and point-mutated antibodies." Proc. Natl. Acad. Sci. USA (1991); 88: 9036-9040.

Clynes, Raphael, "Immune complexes as therapy for autoimmunity". J. Clin. Invest. (2005); 115: 25-27.

Czajkowsky, D.M., et al., "Fc-fusion proteins: new developments and future perspectives". EMBO Molecular Medicine (Oct. 2012); 4(10): 1015-1028. Epub Jul. 26, 2012.

Dalakas, et al., "A Controlled Trial of High-Dose Intravenous Immune Globulin Infusions as Treatment for Dermatomyositis." The New England Journal of Medicine (Dec. 30, 1993); 329(27): 1993-2000.

Davis, et al., "Intermolecular disulfide bonding in IgM: effects of replacing cysteine residues in the heavy chain." EMBO J. (1989); 8 (9): 2519-2526.

De Taeye, et al., "The Ligands for Human IgG and Their Effector Functions". Antibodies (2019); 8(2): 30, 18 pages.

European examination report mailed May 18, 2011 in co-pending European application No. 08769936.9, 7 pages.

Extended European Search Report for European Patent Application No. 17879309.7, dated Jun. 30, 2020, 10 pages.

Extended European Search Report for European Patent Application No. 18166541.5, dated Oct. 18, 2018, 9 pages.

Flanagan, et al., "Soluble Fc Fusion Proteins for Biomedical Research." Meth. Mol. Biol. (2007); 378: 33-52.

Gajdos, et al., "High-Dose Intravenous Gammaglobulin for Myasthenia Gravis." The Lancet (1984); 323 (8373): 406-407.

Ghumra, et al., "Structural requirements for the interaction of human IgM and IgA with the human Fc/ receptor." Eur. J. Immunol. (2009); 39 (4): 1147-1156.

Gliknik website. www.gliknik.com/research/stradomer.php, 2012.

Goldenberg, "Multiple Sclerosis Review." P&T (2012); 37(3): 175-184.

Greenwood et al., "Engineering multiple domains forms of the therapeutic antibody CAMPATH-1H: Effect on complement Lysis," Ther. Immunol. (1994); 1(5):247-255.

Hsieh, et al., "The role of complement component 3 (C3) in differentiation of myeloid-derived suppressor cells". Blood (Mar. 7, 2013); 121(10): 1760-1768. Epub Jan. 8, 2013.

Huang, et al., "In vitro study of combination of rhOPG-Fc and alendronate on inhibition osteoclast." Zhonghua Wai Ke Za Zhi (2005); 43(12):812-816. (Abstract Only, Article in Chinese).

Infante, A.J., "Uses (and abuses) of IVIG in immunology, hematology, and rheumatology." Presentation, University of Texas Health Science, Pediatrics Grand Rounds, San Antonio, TX, Feb. 19, 2010, 12 pages.

International Preliminary Report on Patentability for International Application No. PCT/US2017/065400, dated Jun. 11, 2019, 8 pages.

International Preliminary Report on Patentability, mailed Jan. 29, 2013 in International application No. PCT/US2011/045768, 10 pages.

International Preliminary Report on Patentability, PCT appln. No. PCT/US2008/065428, 8 pages, mailed Dec. 1, 2009.

International Search Report and Written Opinion for International Application No. PCT/US2011/045768, 15 pages, mailed Mar. 8, 2012.

(56) References Cited

OTHER PUBLICATIONS

International Search Report and Written Opinion for International Application No. PCT/US2017/065400, mailed Feb. 14, 2018, 11 pages.
International Search Report for PCT/US2008/065428, 5 pages, mailed Feb. 10, 2009.
Jain, et al., "Fully recombinant IgG2a Fc multimers (stradomers) effectively treat collagen-induced arthritis and prevent idiopathic thrombocytopenia purpura in mice." Arthritis Res. Ther. (2012); 14 (4): R192, 12 pages.
Jayne, et al., "Treatment of systemic vasculitis with pooled intravenous immunoglobulin." The Lancet (May 11, 1991); 337(8750): 1137-1139.
Jefferis, et al., "Interaction sites on human IgG-Fc for FcR: current models." Immunol. Lett. (2002); 82 (1-2): 57-65.
Jin and Balthasar, "Mechanisms of Intravenous Immunoglobulin Action in Immune Thrombocytopenia Purpura." Human Immunology (Apr. 2005); 66(4): 403-410.
Kacskovics, et al., "Fc receptors in livestock species." Vet. Immunol. Immunopathol. (2004); 102: 351-362.
Landschulz, et al., "The Leucine Zipper: A Hypothetical Structure Common to a New Class of DNA Binding Proteins." Science (1988); 240: 1759-1764.
LeHoang, et al., "Intravenous immunoglobulin (IVIg) for the treatment of birdshot retinochoroidopathy." Journal Ocular Immunology and Inflammation (Mar. 2000); 8(1): 49-57.
Lund, J. et al., "Multiple interactions of IgG with its core oligosaccharide can modulate recognition by complement and human Fc gamma receptor I and influence the synthesis of its oligosaccharide chains," J Immunol., Dec. 1, 1996, 157(11):4963-4969.
Lutz, et al., "High Doses of Immunoglobulin G Attenuate Immune Aggregate-Mediated Complement Activation by Enhancing Physiologic Cleavage of C3b in C3bn-IgG Complexes". Blood (Jul. 1996); 88(1): 184-193.
Mason, et al., "Reduced Culture Temperature Differentially Affects Expression and Biophysical Properties of Monoclonal Antibody Variants." Antibodies (2014); 3: 253-271.
Mekhaiel, et al., "Polymeric human Fc-fusion proteins with modified effector functions." Scientific Reports (2011); 1: 124, pp. 1-11.
Mihaesco and Seligmann, "Papain Digestion Fragments of Human IGM Globulins." Journal of Experimental Medicine (1968); 127 (3): 431-453.
Nimmerjahn and Ravetch, "Fc receptors as regulators of immune responses." Nature Reviews Immunology (2008); 8: 34-47.
Ong, et al., "How to accelerate the endothelialization of stents." Arch Mal Coeur Vaiss (2005); 98 (2): 123-126.
Opposition Proceedings No. 2012392760 (Australian Patent Application No. 2012392760 in the name of Liverpool School of Tropical Medicine) filed by Gliknik, Inc. on Jan. 2, 2019, Applicant's Evidence in Answer, Declaration of Dr Beate Peter (and Exhibits BP1-BP9) dated Jul. 2, 2019, and filed Jul. 3, 2019, 147 pages.
Opposition Proceedings No. 2012392760 (Australian Patent Application No. 2012392760 in the name of Liverpool School of Tropical Medicine) filed by Gliknik, Inc. on Jan. 2, 2019, Applicant's Evidence in Answer, Declaration of Sarah Cox (and Exhibit SC1), dated Jul. 2, 2019, and filed Jul. 3, 2019, 36 pages.
Opposition Proceedings No. 2012392760 (Australian Patent Application No. 2012392760 in the name of Liverpool School of Tropical Medicine) filed by Gliknik, Inc. on Jan. 2, 2019, Evidence in Answer in Opposition, Declaration of Anthony Lawrence Shaw (and exhibits ALS-18 and ALS-19 and exhibits ALS-18 and ALS-19) dated and filed Sep. 4, 2019, 14 pages.
Opposition Proceedings No. 2012392760, Notice of Opposition filed by Gliknik, Inc. on Oct. 2, 2018, in Australian Patent Application No. 2012392760 in the name of Liverpool School of Tropical Medicine, 2 pages.
Opposition Proceedings No. 2012392760, Statement of Grounds and Particulars of Opposition filed by Gliknik, Inc. on Jan. 2, 2019, in Australian Patent Application No. 2012392760 in the name of Liverpool School of Tropical Medicine, 11 pages.
Partial European Search Report, EP appl. No. 13169230.3, dated Jul. 31, 2013, 8 pages.
Proceedings of the 126th Annual Meeting of the Pharmaceutical Society of Japan, No. 126 2006, p. 107 (P28[S]am-551) (and Machine translation of pertinent portions), 4 pages.
Reeck, et al., ""Homology" in proteins and nucleic acids: a terminology muddle and a way out of it." Cell (Aug. 1987); 50(5): 667.
Reff and Heard, "A review of modifications to recombinant antibodies: attempt to increase efficacy in oncology applications." Crit. Rev. Oncol./Hematol. (2001); 40: 25-35.
Rowley, et al., "Engineered hexavalent Fc proteins with enhanced Fc-gamma receptor avidity provide insights into immune-complex interactions." Communications Biology (2018); 1: 146, pp. 1-12.
Rütter and Luger, "High-dose intravenous immunoglobulins: An approach to treat severe immune-mediated and autoimmune diseases of the skin". J Am Acad Dermatol. (Jun. 2001); 44(6): 1010-1024.
Rudnick and Adams, "Affinity and Avidity in Antibody-Based Tumor Targeting." Cancer Biotherapy and Radiopharmaceuticals (2009); 24 (2): 155-161.
Salfeld, "Isotype selection in antibody engineering." Nat. Biotechnol. (2007); 25: 1369-1372.
Samuelsson, A., et al., "Anti-inflammatory Activity of IVIG Mediated Through the Inhibitory Fc Receptor." Science (Jan. 2001); 291(5503): 484-486.
Schmidt, et al., "Release of iC3b from apoptotic tumor cells induces tolerance by binding to immature dendritic cells in vitro and in vivo". Cancer Immunol Immunother. (Jan. 2006); 55(1): 31-38.
Schuurman, et al., "The inter-heavy chain disulfide bonds of IgG4 are in equilibrium with intra-chain disulfide bonds." Mol. Immunol. (2001); 38: 1-8.
Shields, et al., "High Resolution Mapping of the Binding Site on Human IgG1 for FcRI, FcrII, FcrIII, and FcRn and Design of IgG1 Variants with Improved Binding to the FcR*," J. Biol. Chem. (2001); 276: 6591-6604.
Simon and Spath, "IVIG—mechanisms of action". Allergy (Jul. 2003); 58(7): 543-552.
Siragam, et al., "Intravenous immunoglobulin ameliorates ITP via activating Fc receptors on dendritc cells." Nature Med. (2006); 12(6):668-692.
Smith, et al., "Addition of a-tailpiece to lgG results in polymeric antibodies with enhanced effector functions including complement-mediated cytolysis by IgG4." J. Immunol. (1995); 154: 2226-2236.
Sørensen, et al., "Effect of the IgM and IgA secretory tailpieces on polymerization and secretion of IgM and IgG." The Journal of Immunology (Apr. 1996); 156(8): 2858-2865.
Stegall, et al., "Terminal Complement Inhibition Decreases Antibody-Mediated Rejection in Sensitized Renal Transplant Recipients." American Journal of Transplantation (2011); 11 (11): 2405-2413. Epub Sep. 22, 2011.
Stewart, R., et al., "The role of Fc gamma receptors in the activity of immunomodulatory antibodies for cancer." Journal for Immuno Therapy of Cancer (2014); 2: 29, 10 pages.
Sultan, et al., "Anti-idiotypic suppression of autoantibodies to factor VIII (antihaemophilic factor) by high-dose intravenous gammaglobulin." The Lancet (Oct. 6, 1984); 2(8406): 765-768.
Sun, et al., "Recombinant human IgG1 based Fe multimers, with limited FcR binding capacity, can effectively inhibit complement-mediated disease." Journal of Autoimmunity (Nov. 2017); 84: 97-108. Epub Aug. 19, 2017.
Supplemental European Search Report for European Application No. 08769936.9, dated May 26, 2010, 9 pages.
Supplemental European Search Report for European Application No. 11813204.2, dated Jul. 3, 2015, 6 pages.
Teeling, et al., "Therapeutic efficacy of intravenous immunoglobulin preparations depends on the immunoglobulin G dimers: studies in experimental immune thrombocytopenia." Blood (2001); 98 (4): 1095-1099.
Thiruppathi, et al., "Recombinant IgG2a Fc (M045) multimers effectively suppress experimental autoimmune myasthenia gravis." J. Autoimmunity (2014); 52 (2): 64-73.

(56) References Cited

OTHER PUBLICATIONS

Van Der Mech, et al., "A Randomized Trial Comparing Intravenous Immune Globulin and Plasma Exchange in Guillain-Barr Syndrome." The New England Journal of Medicine (Apr. 23, 1992); 326(17): 1123-1129.

Van Noort and Amor, "Cell Biology of Autoimmune Diseases." International Review of Cytology (1998); 178: 127-205.

Vidarsson, et al., "IgG subclasses and allotypes: from structure to effector functions." Frontiers in Immunology (2014); 5 (1): 1-17.

Wei, Xiaoshan et al., "Proteomics studies of autoimmune diseases of the nervous system." Journal of Apoplexy and Nervous Diseases (2009); vol. 26, No. 5, pp. 630-632, and English summary / abstract, 4 pages.

White, D.M., et al., "Design and expression of polymeric immunoglobulin fusion proteins: a strategy for targeting low-affinity Fc gamma receptors." Protein Expression and Purification (Apr. 2001); 21(3): 446-455.

Written Opinion of the International Searching Authority, PCT appln. No. PCT/US2008/065428, 7 pages, mailed Feb. 11, 2009.

Yoo, et al. "Human IgG2 can form covalent dimers." The Journal of Immunology (2003); 170 (6): 3134-3138.

Zhou, et al., "A fully recombinant human IgG1 Fc multimer (GL-2045) inhibits complement-mediated cytotoxicity and induces iC3b". Blood Adv. (Mar. 14, 2017); 1(8): 504-515. eCollection Mar. 14, 2017.

Zuercher, et al., "IVIG in autoimmune disease—Potential next generation biologics". Autoimmun Rev. (Aug. 2016); 15(8):781-785. Epub Mar. 25, 2016.

*p < 0.005 all time points*

METHODS OF TREATING INFLAMMATORY DISORDERS WITH MULTIVALENT FC COMPOUNDS

REFERENCE TO RELATED APPLICATIONS

This application is a divisional of U.S. patent application Ser. No. 16/467,859, filed Jun. 7, 2019, now U.S. Pat. No. 11,331,372, which is the U.S. national stage application of International Patent Application No. PCT/US2017/065400, filed Dec. 8, 2017, claims the benefit of priority to U.S. Provisional Patent Application No. 62/432,407, filed Dec. 9, 2016, the contents of which are incorporated herein by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: GLIK_020_02US_ST25.txt, date recorded: Jun. 24, 2020, file size 9.07 kilobytes).

FIELD OF THE INVENTION

This invention relates generally to the fields of immunology, autoimmunity, inflammation, and tumor immunology. More specifically, the present invention relates to methods for determining a patient's response to multi-Fc therapeutics and methods for determining an effective dose of a multi-Fc therapeutic. The invention further relates to treating pathological conditions such as autoimmune and inflammatory diseases.

BACKGROUND OF THE INVENTION

Immunoglobulin products from human plasma have been used since the early 1950's to treat immune deficiency disorders, and more recently for autoimmune and inflammatory disease. Human IVIG (IVIG) is a formulation of sterile, purified immunoglobulin G (IgG) products manufactured from pooled human plasma that typically contains more than 90% unmodified IgG, with only small and variable amounts of the aggregated immunoglobulins, IgA or IgM (Rutter A et al., J Am Acad Dermatol, 2001, June; 44(6): 1010-1024). IVIG was initially used as an IgG replacement therapy to prevent opportunistic infections in patients with low IgG levels (Baerenwaldt, Expert Rev Clin Immunol, 6(3), p 425-434, 2010). Today the most common use of IVIG is in the treatment of chronic inflammatory demyelinating polyneuropathy and, in addition to use in primary and secondary immunodeficiencies, it is licensed for the treatment of autoimmune diseases including idiopathic thrombocytopenic purpura (ITP), chronic inflammatory demyelinating polyneuropathy (CIDP), multifocal motor neuropathy (MMN), Guillain-Barre syndrome, and Kawasaki disease. IVIG also has an established role in other autoimmune diseases including the inflammatory myopathies (polymyositis, dermatomyositis, and inclusion body myositis), Eaton-Lambert syndrome, myasthenia gravis, and stiff person syndrome.

It has been observed that traces (1-5%) of IgG are present as aggregated forms within IVIG, and IgG dimers can make up approximately 5-15% of IVIG. Preclinical and clinical studies indicate that these aggregated fractions of IVIG are disproportionately effective in the treatment of certain autoimmune diseases mediated by pathologic immune complexes, with most of the activity isolated to the Fc portion of these IVIG aggregates. Thus, the most effective fraction of IVIG, though a small percent of IVIG, is the multi-Fc aggregates (See, Augener et al, Blut, 50, 1985; Teeling et al, Immunobiology, 96, 2001; Bazin et al, British Journal of Haematology, 127, 2004). Alternatives to IVIG therapy using compounds that present polyvalent Fc to Fc Receptors and thus bind even low affinity Fc receptors avidly, similar to IVIG aggregates, have been described (See US Patent Application Publication Nos. 2010/0239633; 2013/0156765; 2015/0218236; 2016/0229913; 2010/0143353, as well as International PCT Application Publication Nos. WO 2017/019565; WO 2015/132364; and WO 2015/132365).

GL-2045, described in US Patent Application Publication No. 2013/0156765, is a multimerizing general stradomer that is a recombinant mimetic of IVIG. GL-2045 binds most or all of the ligands to which immunoglobulin (Ig) G1 Fc binds. Further, GL-2045 binds with high affinity and avidity to all canonical receptors and to complement C1q, and has a 10-1,000 fold greater in vitro efficacy compared to IVIG. As such, GL-2045 also has potential clinical utility in treating a wide range of autoimmune diseases, including but not limited to idiopathic thrombocytopenic purpura (ITP), chronic inflammatory polyneuropathy, multifocal motor neuropathy, myasthenia gravis, organ transplantation, and rheumatoid arthritis.

IVIG is one of the most widely prescribed drugs in physicians' armamentarium but has several drawbacks including high-cost of production, lot-to-lot variability, variable efficacy at any given dose, lack of a biomarker to indicate sufficient dosing for efficacy, 1-2 day infusion times, high protein load, use of nephrotoxic solubilizers, and risk of infectious contamination. Additionally, IVIG is prescribed across a range of doses, generally 0.6-2 g/Kg every 3 to 6 weeks with variable efficacy; approximately 50-75% of patients respond to therapy. Current standards of care lack the ability to predict which patients will or will not respond to a given dose of IVIG. There is also currently no biomarker available to determine when the patient has received an adequate dose of IVIG. The use of synthetic, multi-Fc therapeutics (i.e., GL-2045 and others) overcomes many of the drawbacks of IVIG, while demonstrating increased efficacy and potency. The use of synthetic, recombinantly-produced, multi-Fc therapeutics also substantially reduces the likelihood of aberrant inflammatory responses in the recipient, such as those resulting from the transfer of variable amounts of IgA in different IVIG brands and lots, or the potential transfer of viral (such as Zika) or prion infections. However, the challenges of predicting a given patient's response to a given dose, as well as identifying clinically effective doses, of multi-Fc therapeutics remain.

As with all immunoglobulin products, treatment protocols for multi-Fc therapeutics must balance the risks of inadequate dosing (i.e. failure to effectively treat the underlying disease or disorder) with the risks of excessive dosing or rate of infusion including, in the case of multi-Fc therapeutics, hypotension, fever, renal dysfunction from excess protein load, or excessive and unnecessary cost. As such, there is a need in the art for methods that enable the determination of an effective dose of a multi-Fc product, such that the maximally effective therapeutic dose is achieved with a minimum amount of the multi-Fc product. Such methods will enable the optimization of therapeutically beneficial effects while minimizing the risk of adverse side effects.

SUMMARY OF THE INVENTION

The methods of the current invention provide for the identification of patients with an inflammatory or autoimmune disease that demonstrate an inadequate response to treatment with a multi-Fc therapeutic, and the determination of an optimal dose of a multi-Fc therapeutic for said patient based on the patient's circulating levels of "inactivated C3b", known as iC3b. The methods of the current invention also provide for use of a starting dose of a multi-Fc therapeutic in order to assess the effect of the multi-Fc therapeutic on iC3b levels. The methods of the current invention also provide for other complement components that may be employed as a surrogate for iC3b based on an analogous response to multi-Fc therapeutics. These methods are based, at least in part, on the unexpected findings that levels of iC3b correlate with the in vitro efficacy of a multi-Fc therapeutic and provide for improvements in the use of such therapeutics in the treatment of autoimmune and inflammatory diseases.

In some embodiments, the present invention provides for a method of treating an autoimmune or inflammatory disease in a patient determined to have an inadequate response to a multi-Fc therapeutic comprising administering a first cumulative escalated dose of the multi-Fc therapeutic at a dose of at least about 105% of a starting dose of said multi-Fc therapeutic during a first dosing period, wherein the patient has been determined to have blood levels of iC3b lower than a predetermined threshold following administration with the starting dose of the multi-Fc therapeutic or blood levels of iC3b with a change of less than about 10% from baseline.

In some embodiments, the present invention provides for a method of treating an autoimmune or inflammatory disease in a patient comprising administering a starting dose of a multi-Fc therapeutic, determining the blood level of iC3b in the patient, and determining the adequacy of response to the starting dose of the multi-Fc therapeutic if blood levels of iC3b are higher than a predetermined threshold or have increased by at least 10% from a baseline iC3b measurement.

The methods of the current invention further comprise repeating the determination of blood iC3b levels of the patient after the administration of the first cumulative escalated dose of the multi-Fc therapeutic and administering a second cumulative escalated dose of the multi-Fc therapeutic for a second dosing period that is higher than the previously administered dose if the levels of iC3b are determined to be lower than a predetermined threshold, or blood levels of iC3b with a change of less than about 10% from baseline. In some embodiments, the repeated measurements of iC3b and administration of additional cumulatively escalated doses of the multi-Fc therapeutic are continued until the predetermined iC3b threshold is met or until blood levels of iC3b have changed by greater than about 10% from baseline.

In some aspects, the present invention provides methods comprising (a) administering the multi-Fc therapeutic to a subject in need thereof at a starting dose for said multi-Fc therapeutic; (b) measuring the level of circulating iC3b in the subject; (c) determining that the subject requires a first cumulative escalated dose of the multi-Fc therapeutic when the circulating level of iC3b in the subject is below a predetermined threshold, or blood levels of iC3b with a change of less than about 10% from baseline; and (d) administering a first cumulative escalated dose of the multi-Fc therapeutic. In further embodiments, the methods providing herein for determining the effective dose of a multi-Fc therapeutic further comprise (e) repeating the determination of a blood iC3b level of the patient after administration of the first cumulative escalated dose of the multi-Fc therapeutic; and (f) administering a second cumulative escalated dose of the multi-fc therapeutic that is higher than the previously administered cumulative escalated dose if the level of iC3b is lower than a predetermined threshold, or blood levels of iC3b with a change of less than about 10% from baseline. In some embodiments, the determinations of iC3b and administrations of cumulative escalated doses are repeated until the predetermined iC3b threshold is met or until blood levels of iC3b have changed by greater than about 10% from baseline.

In some embodiments, the cumulative escalated dose comprises administering an escalated dose of the multi-Fc therapeutic throughout the dosing period. In some embodiments, the cumulative escalated dose comprises administering both an escalated dose and one or more incremental dose during the dosing period.

In some embodiments, the multi-Fc therapeutic comprises (a) a first polypeptide comprising a first Fc domain monomer, a linker, and a second Fc domain monomer; (b) a second polypeptide comprising a third Fc domain monomer; and (c) a third polypeptide comprising a fourth Fc domain monomer, wherein said first Fc domain monomer and said third Fc domain monomer combine to form a first Fc domain and said second Fc domain monomer and said fourth Fc domain monomer combine to form a second Fc domain.

In some embodiments, the multi-Fc therapeutic comprises (a) a polypeptide comprising at least a first and second Fc fragment of IgG; and (b) at least one of said first Fc fragments of IgG comprising at least one CH2 domain and at least one hinge region, wherein the first and second Fc fragments of IgG being bound through the at least one hinge region to form a chain, wherein the polypeptide further comprises multiple substantially similar chains bound to at least one other of said multiple chains in a substantially parallel relationship to form a dimer. In further embodiments, the multiple parallel chains form a multimer.

In some embodiments, the multi-Fe therapeutic comprises a polypeptide comprising two or more Fc domains, wherein each Fc domain is comprised of two Fc domain monomers, wherein each Fc domain monomer is comprised of (a) a CH1 and a CH2 domain; (b) an N-terminal hinge region; and (c) a multimerization domain fused to the C-terminus; and wherein the multimerization domain causes the Fc domains to assemble into a multimer. In further embodiments, the multimerization domain is derived from IgM or IgA.

In some embodiments, the multi-Fe therapeutic comprises two or more polypeptides each comprising at least one Fc domain bound to a core moiety, wherein each Fc domain is comprised of two Fc domain monomers each comprised of (a) a CH1 and a CH2 domain; (b) an N-terminal hinge region. In some embodiments, the core moiety is a polystyrene bead. In some embodiments, each of the Fc domains further comprise an IgM CH4 domain and the core moiety comprises a J-chain resulting a biomimetic capable of binding multiple Fcγ receptors.

In some embodiments, the multi-Fe therapeutic comprises five or six Fc domain polypeptides, wherein each Fc domain polypeptide comprises two Fc domain monomers each comprising a cysteine residue linked via a disulfide bond to a cysteine residue to an adjacent Fc domain polypeptide and a multimerization domain, wherein the multimerization domain causes the Fc domain polypeptides to assemble into a multimer. In further embodiments, the multimerization domain is derived from IgM or IgA.

In some embodiments, the multi-Fe therapeutic comprises three, four, five, or six Fc domains.

In some embodiments, the multi-Fe therapeutic comprises an aggregated immunoglobulin fraction of intravenous immunoglobulin (IVIG). In some embodiments, the multi-Fe therapeutic comprises GL-2045.

In some embodiments, the cumulative escalated dose of the multi-Fe therapeutic is at least about 110% of the starting dose of the multi-Fe therapeutic. In some embodiments, the cumulative escalated dose is at least about 115%, 120%, 125%, 150%, 175%, or 200% of the starting dose of the multi-Fe-therapeutic.

In some embodiments, the predetermined threshold of iC3b below which an additional dose of a multi-Fe therapeutic is administered is about 25 µg/mL to 300 µg/mL above assay background. In further embodiments, the predetermined threshold of iC3b below which an additional dose of a multi-Fe therapeutic is administered is about 50 µg/mL to 200 µg/mL above assay background. In further embodiments, the predetermined threshold of iC3b below which an additional dose of a multi-Fc therapeutic is administered is about 75 µg/mL to 125 µg/mL above assay background. In still further embodiments, the predetermined threshold of iC3b below which an additional dose of a multi-Fc therapeutic is administered is 100 µg/mL above assay background. In some embodiments, the predetermined threshold of iC3b below which an additional dose of a multi-Fc therapeutic is administered is about 25% of neutrophils and monocytes that are iC3b+. In some embodiments, the percent change of iC3b levels is less than about 20% from baseline. In some embodiments, the percent change of iC3b levels is less than about 30% from baseline. In some embodiments, the percent change of iC3b levels is less than about 40% from baseline. In some embodiments, the percent change of iC3b levels is less than about 50% from baseline.

In some embodiments, the iC3b level is determined by measurement of iC3b1 and/or iC3b2. In some embodiments, the level of iC3b is determined by measurement of an iC3b surrogate marker. In some embodiments, the iC3b surrogate marker is selected from the group consisting of C3a, C3a desArg, C4a, C4a desArg, C3f, C3c, C3dg, C3d, and C3g. In some embodiments, the predetermined threshold for the iC3b surrogate marker is less than about 30 ng/mL. In some embodiments, the predetermined threshold for the iC3b surrogate marker is less than about 20 ng/mL. In some embodiments, the predetermined threshold for the iC3b surrogate marker is less than about 10 ng/mL. In some embodiments, the predetermined threshold for the iC3b surrogate marker is less than about 5 ng/mL. In some embodiments, the percent change of the iC3b surrogate marker is less than about 10%. In some embodiments, the percent change of the iC3b surrogate marker is less than about 20%. In some embodiments, the percent change of the iC3b surrogate marker is less than about 30%. In some embodiments, the percent change of the iC3b surrogate marker is less than about 40%. In some embodiments, the percent change of the iC3b surrogate marker is less than about 50%.

In further embodiments, the predetermined threshold of iC3b below which an additional dose of a multi-Fc therapeutic is administered is an iC3b MFI of about 125% of the baseline iC3b MFI. In some embodiments, the iC3b level is determined by an immunoassay. In further embodiments, the immunoassay is an ELISA or a western blot. In some embodiments, the iC3b level is determined by flow cytometry.

In some embodiments, a patient is determined to have an inadequate response to a multi-Fc therapeutic when the patient has a blood level of iC3b that has changed less than 10% from the patient's baseline iC3b levels. In some embodiments, a patient is determined to have an inadequate response to a multi-Fc therapeutic when the patient has a blood level of iC3b or an iC3b surrogate that has changed less than 10% from the patient's previous iC3b or iC3b surrogate levels (e.g., a change of less than 10% from iC3b levels determined after administration of a cumulative escalated dose). In some embodiments, the patient's blood levels have changed less than 15%. In some embodiments, the patient's blood levels have changed less than 20%. In further embodiments, the patient's blood levels have changed less than 50%, less than 100%, less than 200%, or more.

In some embodiments, the methods of the present invention are used in the treatment of an autoimmune or inflammatory disease. In further embodiments the autoimmune or inflammatory disease is selected from a group consisting of autoimmune cytopenia, idiopathic thrombocytopenic purpura, rheumatoid arthritis, systemic lupus erythematosus, asthma, Kawasaki disease, Guillain-Barre syndrome, Stevens-Johnson syndrome, Crohn's colitis, diabetes, chronic inflammatory demyelinating polyneuropathy, myasthenia gravis, anti-Factor VIII autoimmune disease, dermatomyositis, vasculitis, uveitis and Alzheimer's disease.

DETAILED DESCRIPTION OF THE INVENTION

Figure 1A:
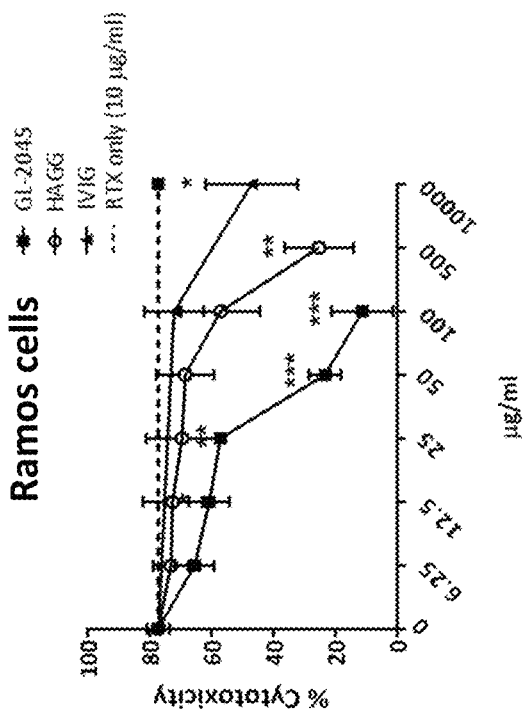
FIG. 1A-FIG. 1B illustrate GL-2045, HAGG, and IVIG inhibition of rituximab-induced, complement-dependent cytotoxicity (CDC) of SUDHL4 and Ramos cells.

Provided herein are methods for the treatment of autoimmune and inflammatory diseases that include first determining an inadequate immune response in a patient treated with a multi-Fc therapeutic based on blood levels of inactivated C3b (iC3b). Second, subsequent and increasing doses of a multi-Fc therapeutic are administered and blood levels of iC3b, or an iC3b surrogate, are measured in order to determine a therapeutically effective dose of the multi-Fc therapeutic in a given patient at a given point in time. These methods are based on the unexpected finding that iC3b levels correlated with GL-2045, G994, and G998 efficacy. The methods provided herein have utility for treating autoimmune disease, inflammatory disease, allergy, antibody-mediated disease, and complement-mediated disease.

As used herein, the use of the word "a" or "an" when used in conjunction with the term "comprising" in the claims and/or the specification may mean "one," but it is also consistent with the meaning of "one or more," "at least one," and "one or more than one." All references cited herein are incorporated by references in their entireties.

Complement Activation and iC3b

The methods of the present invention comprise, in part, measuring activation of the complement cascade and generation of specific complement cleavage and/or degradation products (e.g., iC3b) to determine a patient's response to a multi-Fc therapeutic. Some of the multi-Fc therapeutics described herein are capable, at a minimum, of presenting multivalent Fc to complement components. In some embodiments, the multi-Fc therapeutics described herein are capable of presenting multivalent Fc to both canonical Fc receptors (e.g., FcγRI, FcγRIIa, FcγRIIb, or FcγRIII) and complement components, and some of the multi-Fc therapeutics described herein are capable of presenting multivalent Fc primarily to complement components and not to low affinity Fc receptors. As used herein, the term "complement" refers to any of the proteins of the complement cascade, sometimes referred to in the literature as the complement system or complement cascade. As used herein, the terms "complement binding" or "binding to complement" refer to binding of any of the components of the complement cascade. Components of the complement cascade are known in the art and described, for example, in Janeway's Immunobiology, 8$^{th}$ Ed., Murphy ed., Garland Science, 2012. There are three main complement pathways currently known: the classical pathway, the alternative pathway, and the lectin binding pathway. The classical complement pathway is activated after the protein C1q binds to one or more molecules of intact and bound immunoglobulin IgM, or at least two molecules of intact and bound immunoglobulin IgG1, IgG2, or IgG3, after which C1qC1rC1s is formed and cleaves C4. Complement activation leads to complement-dependent cytolysis (CDC). Excessive complement activation can be detrimental and is associated with many diseases including myasthenia gravis, hemolytic uremic syndrome (HUS), and paroxysmal nocturnal hemoglobinuria (PNH).

The different pathways of complement activation converge on the generation of C3b through the actions of classical C3 convertase (C4bC2a) or alternative C3 convertase (C3bBb). C3b itself is a critical component of the alternative C3 convertase, as well as the classical and alternative C5 convertases, each of which mediates downstream complement activation. The half-life of C3b is believed to be less than a second unless stabilized by binding to another protein. C3b can be stabilized a number of ways, including formation of C3b-C3b-IgG covalent complexes, binding to the C4bC2a complex to generate classical C5 convertase (C4bC2aC3b), microbial or host cell-surface opsonization leading to C3 convertase (C3bBb) generation through associations with Factor B and cleavage by Factor D, and combining with already-formed C3 convertase (C3bBb) to form alternative C5 convertase (C3bBbC3b).

If unbound, C3b is degraded to "inactivated" C3b or "iC3b", facilitated in part by the actions of both Factor H and Factor I. Cleavage of C3b between Arg1281-Ser1282 results in the inactivation of C3b to iC3b1. Further cleavage between Arg1298-Ser1299 results in the release of C3f from iC3b1 and generates iC3b2. As used herein, iC3b may refer to either iC3b1 and/or iC3b2 and measurement of iC3b may detect either iC3b1 or iC3b2, or may detect both iC3b1 and iC3b2. In some embodiments, iC3b may be further degraded into C3c and C3dg, and C3dg may be further degraded into C3d and C3g. The terms "iC3b generation" and "production of iC3b" are used interchangeably herein and refer to what the scientific literature describes as the inactivation of C3b enhanced by Factor H and Factor I to result in the presence of or change in a level of iC3b (e.g., the inactivation of C3b enhanced by Factor H and/or Factor I). Despite its name, iC3b is not biologically inactive. Unlike active C3b, generation of iC3b inhibits downstream complement activation in two ways. First, cleavage of C3b, enhanced by Factor H and Factor I activity, into iC3b limits the amount of C3b available for the formation of C5 convertase, thus limiting the generation of downstream inflammatory complement products such as C5a and the membrane attack complex (MAC) (also called sc5b-9 or the terminal complement complex (TCC)). Second, unlike C3b, iC3b is unable to bind to Factor B, thereby limiting the formation of additional C3 convertase during alternative complement activation and preventing the complement activation loop.

Although some studies have described iC3b as an activation fragment indicative of pathologic complement activation (See, Olson et al, U.S. Pat. No. 9,164,088), iC3b is well documented to have potent anti-inflammatory and tolerogenic properties. For instance, iC3b binding to complement receptor 3 (CR3) reduced monocyte differentiation into dendritic cells and mediated long lasting tolerogenic responses (Schmidt et al., Cancer Immunol Immunother., 55(1), pp. 31-38, (2006)). iC3b also promoted the generation of myeloid-derived suppressor cells (MDSC) (Hsieh et al., Blood, 121(10), pp. 1760-1768, (2013)) and promoted induction of TGFβ32 and IL-10 (See Amarilyo et al., Eur J Immunol., 40(3), pp. 699-709, (2010)). Additionally, in contrast to the ultra-short half-life of C3b, iC3b has a relatively long half-life of 30-90 minutes, suggesting the ability of iC3b to mediate sustained anti-inflammatory responses.

The present inventors have unexpectedly found that levels of circulating iC3b and complement components that change in parallel with iC3b (i.e., iC3b surrogates), are indicative of the relative therapeutic efficacy of multi-Fc therapeutics (e.g., GL-2045, G994, G998, IVIG, SIF3™). Thus, in stark contrast to the teachings of Olson et al, data described herein indicates that higher levels of iC3b are desirable in the treatment of autoimmune and inflammatory disorders. As iC3b generation generally requires initial activation of the complement cascade and is not anticipated to occur to any significant degree in the absence of complement activation, it therefore follows that initial complement activation is desirable in treating autoimmune and inflammatory disorders with multi-Fc therapeutics, despite generations of teachings that complement cascade activation is deleterious in autoimmune and inflammatory disorders. Monoclonal antibody or small molecule approaches to blocking upstream classical pathway complement activation, such as the use of monoclonal antibodies targeting C1q, C1r, or C1s, would inhibit initiation of complement activation and would therefore not generate the long-lived, anti-inflammatory iC3b. Similarly, anti-C5 monoclonal antibodies or small molecule approaches to blocking downstream complement activation, such as the use of monoclonal antibodies or small molecules targeting C5, would not be expected to initiate complement activation and would therefore not generate the long-lived, anti-inflammatory iC3b. In contrast, multi-Fc therapeutics including IVIG aggregates and the recombinant biomimetics described herein, which present multiple functional Fc to hexameric C1q, will initiate upstream complement activation as well as generation of anti-inflammatory iC3b by subsequently blocking downstream activation of the complement cascade at the level of C3/C3b.

The initial activation of the complement cascade observed with multi-Fc therapeutics is followed by subsequent inhibition of the complement cascade and is associated with inhibition of CDC. Data herein demonstrate that iC3b generation is dependent on both the initial activation and subsequent shutting down of the complement cascade. As such, the generation of iC3b is accompanied by (1) generation of upstream complement cleavage products (such as C3a and C4a), and (2) inhibition of downstream effector mechanisms, such as CDC, with only small amounts of C5a and the TCC generated. The amount of C5a and TCC generated are generally about two-fold above baseline values and may remain within the normal range despite being increased over baseline.

In some embodiments, iC3b may be in the form of iC3b1, generated by cleavage of C3b between Arg1281-Ser1282. In some embodiments, iC3b may be in the form of iC3b2, generated by cleavage of iC3b1 to produce iC3b2 and C3f. In some embodiments, assessment of iC3b levels comprises detection of iC3b1 and/or iC3b2. In some embodiments, assessment of iC3b levels comprises detection or measurement of an iC3b surrogate. Herein, the terms "iC3b surrogate" and "iC3b surrogate marker" are used interchangeably and refer to a component of the complement cascade, or a component of iC3b itself, the levels of which correlate with the levels of iC3b. iC3b surrogates include iC3b cleavage products including C3f, C3c, C3dg, C3d, and/or C3g, as well as upstream complement cleavage products including C3a, C3a desarg, C4a, and/or C4a desarg.

Figure 9:
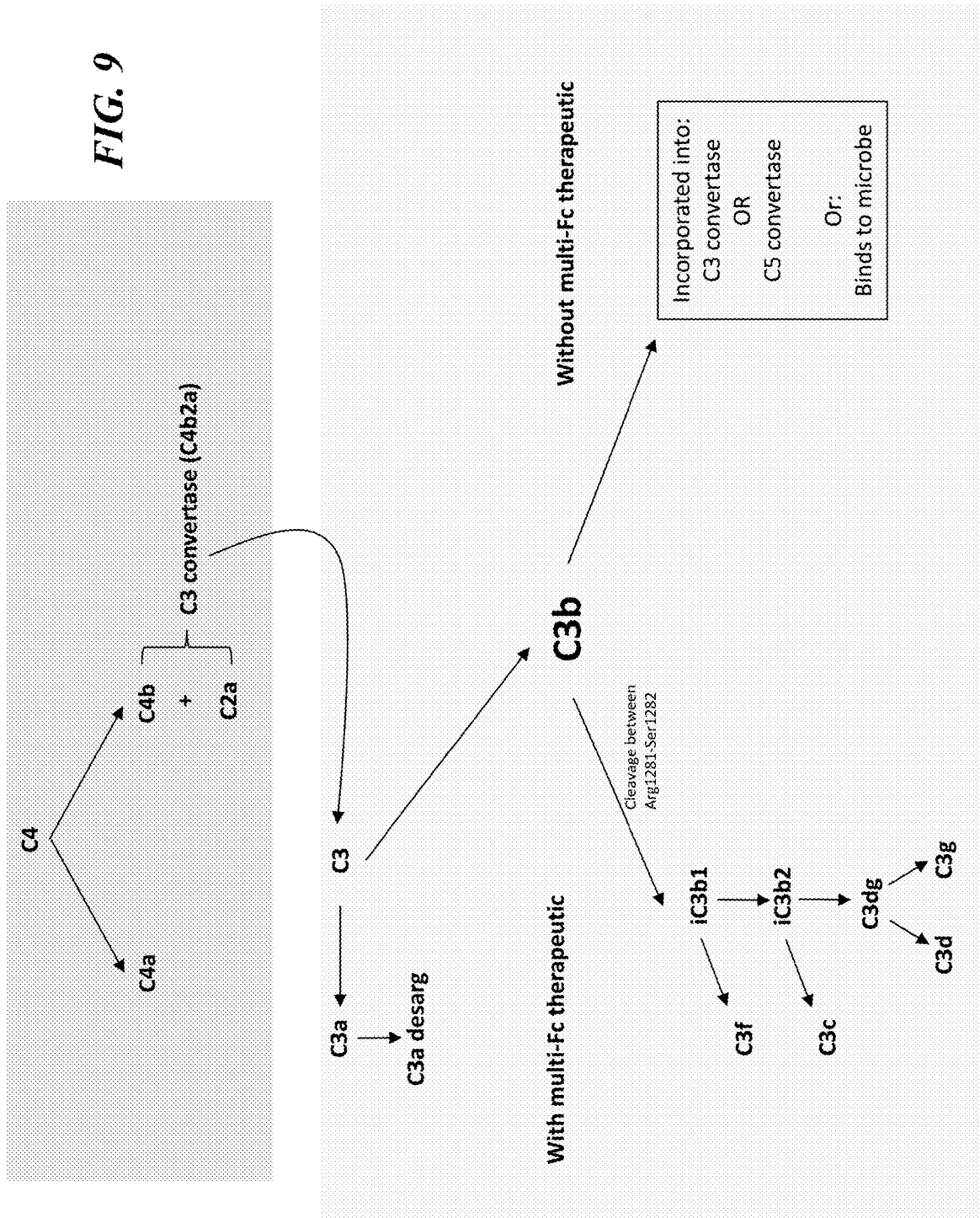
FIG. 9 illustrates the relationship on a molar basis among iC3b and various surrogate markers of iC3b that can be used in the testing and dosing of multi-Fc therapeutics.

A schematic of the relationship on a molar basis among iC3b and various surrogate markers of iC3b is provided in FIG. 9. Cleavage of C3 by C3 convertase generates equimolar amounts of the C3 cleavage products C3a and C3b. As described above, C3b is unstable and is degraded to iC3b in less than a second if not stabilized. If the generation of stable C3b is inhibited (i.e., by treatment with a multi-Fc therapeutic), cleavage of C3 will result in the generation of equimolar amounts of C3a and iC3b. Therefore, in the context of multi-Fc therapeutics that both activate the complement cascade and inhibit generation of stable C3b, and in the absence of infection or other force that stabilizes C3b, levels of C3a will increase proportionally with levels of iC3b. In such instances, measurements of C3a can be used as a surrogate for measurements of iC3b. Additionally, biologically active C3a may be catabolized to the less active, but more stable, C3a desArg (also called acylation stimulating protein (ASP)) by the removal of the C-terminal arginine. Therefore, in some embodiments, the level C3a desArg may be used as a surrogate to determine a patient's levels of downstream of iC3b. In some embodiments, the combined levels of C3a and C3a desArg may be used as a surrogate for downstream iC3b levels. In further embodiments, levels of C4a and/or C4a desArg are used as a surrogate for iC3b levels to determine whether or not a patient's iC3b levels are below a predetermined threshold or whether a patient's iC3b levels have a less than 10% change from a baseline level. In some embodiments, the C3a/C3a desArg measurements are conducted between 30 minutes and 12 days or more after administration of a starting dose. In some embodiments, a change in C3a and/or C3a desArg levels of less than 50% from a patient's baseline levels is indicative of an inadequate response to a multi-Fc therapeutic. In some embodiments, a change in C3a and/or C3a desArg levels of less than 40% from a patient's baseline levels is indicative of an inadequate response to a multi-Fc therapeutic. In some embodiments, a change in C3a and/or C3a desArg levels of less than 30% from a patient's baseline levels is indicative of an inadequate response to a multi-Fc therapeutic. In some embodiments, a change in C3a and/or C3a desArg levels of less than 20% from a patient's baseline levels is indicative of an inadequate response to a multi-Fc therapeutic. In some embodiments, a change in C3a and/or C3a desArg levels of less than 10% from a patient's baseline levels is indicative of an inadequate response to a multi-Fc therapeutic.

Similar embodiments are contemplated for C4a and its degradation product, C4a desArg. iC3b generally cannot be generated in the absence of complement activation. As C4 is cleaved to C4a and C4b upon activation of the classical pathway, C4b is incorporated into the C3 convertase for the classical and lectin pathways. The present inventors have also found that, upon activation of the classical pathway by a multi-Fc therapeutic, the expected and desirable C4a generation that is a byproduct of activation of the classical pathway corresponds to iC3b generation. Without being bound by theory, it is thought that this is because a multi-Fc therapeutic (e.g., IVIG or GL-2045) initially activates the classical complement pathway after which complement activation is terminated primarily at the level of C3/C3b, thus generating iC3b. Generation of C4a and/or the C4a degradation product, C4a desArg, or the combination of C4a and C4a desArg, indicate classical pathway activation and, in the context of a multi-Fc therapeutic that blocks complement activation at the level of C3/C3b, are also surrogates for adequate generation of iC3b. As such, in some embodiments, levels of C4a and/or C4a desArg may be used as a surrogate for downstream iC3b levels. In further embodiments, the combined levels of C4a and C4a desArg may be used as a surrogate for downstream iC3b levels.

In further embodiments, levels of C4a and/or C4a desArg are used as a surrogate for iC3b levels to determine whether or not a patient's iC3b levels are below a predetermined threshold or whether a patient's iC3b levels have a less than 10% change from a baseline level. In some embodiments, the C4a/C4a desArg measurements are conducted between 5 minutes and 96 hours after administration of a starting dose. In some embodiments, a change in C4a and/or C4a desArg levels of less than 50% from a patient's baseline levels is indicative of an inadequate response to a multi-Fc therapeutic. In some embodiments, a change in C4a and/or C4a desArg levels of less than 40% from a patient's baseline levels is indicative of an inadequate response to a multi-Fc therapeutic. In some embodiments, a change in C4a and/or C4a desArg levels of less than 30% from a patient's baseline levels is indicative of an inadequate response to a multi-Fc therapeutic. In some embodiments, a change in C4a and/or C4a desArg levels of less than 20% from a patient's baseline levels is indicative of an inadequate response to a multi-Fc therapeutic. In some embodiments, a change in C4a and/or C4a desArg levels of less than 10% from a patient's baseline levels is indicative of an inadequate response to a multi-Fc therapeutic.

Multi-Fc Therapeutics

As used herein, the terms "biomimetic", "biomimetic molecule", "biomimetic compound", and related terms refer to a human made compound that imitates the function of another naturally occurring compound, such as IVIG, a monoclonal antibody, or the Fc fragment of an antibody. "Biologically active" biomimetics are compounds which possess biological activities that are the same as or similar to their naturally occurring counterparts. By "naturally occurring" is meant a molecule or portion thereof that is normally found in an organism. By naturally occurring is also meant substantially naturally occurring. "Immunologically active" biomimetics are biomimetics which exhibit immunological activity the same as or similar to naturally occurring immunologically active molecules, such as antibodies, cytokines, interleukins, and other immunological molecules known in the art. In preferred embodiments, the biomimetics for use in the present invention are multi-Fc therapeutics (e.g. stradomers) as defined herein.

The term "isolated" polypeptide or peptide as used herein refers to a polypeptide or a peptide which either has no naturally-occurring counterpart or has been separated or purified from components which naturally accompany it, e.g., in tissues such as pancreas, liver, spleen, ovary, testis, muscle, joint tissue, neural tissue, gastrointestinal tissue, or breast tissue or tumor tissue (e.g., breast cancer tissue), or body fluids such as blood, serum, or urine. Typically, the polypeptide or peptide is considered "isolated" when it is at least 70%, by dry weight, free from the proteins and other naturally-occurring organic molecules with which it is naturally associated. Preferably, a preparation of a polypeptide (or peptide) of the invention is at least 80%, more preferably at least 90%, and most preferably at least 99%, by dry weight, the polypeptide (peptide) of the invention. Since a polypeptide or peptide that is chemically synthesized is inherently separated from the components that naturally accompany it, the synthetic polypeptide or peptide is "isolated." An isolated polypeptide (or peptide) of the invention can be obtained, for example, by expression of a recombinant nucleic acid encoding the polypeptide or peptide or by chemical synthesis. A polypeptide or peptide that is produced in a cellular system different from the source from which it naturally originates is "isolated" because it will necessarily be free of components which naturally accompany it. In a preferred embodiment, the isolated polypeptide of the current invention contains only the sequences corresponding to the IgG1 Fc monomer and the IgG2 hinge multimerization domain (SEQ ID NO: 1), and no further sequences that may aid in the cloning or purification of the protein (e.g., introduced restriction enzyme recognition sites or purification tags). The degree of isolation or purity can be measured by any appropriate method, e.g., column chromatography, polyacrylamide gel electrophoresis, or HPLC analysis.

As used herein, a "multi-Fc therapeutic" refers to a biomimetic protein capable of, at a minimum, presenting multivalent (i.e., two or more) Fc to components of the complement system. In some embodiments, the multi-Fc therapeutics described herein are capable of presenting multivalent Fc to both canonical Fc receptors (e.g., FcγRI, FcγRIIa, FcγRIIb, FcγRIIIa, and/or FcγRIIIb) and complement components. The multi-Fc therapeutic may be multimerized or not. Multi-Fc therapeutics used in accordance with the methods described herein may refer to general multi-Fc compounds, such as those disclosed in US Patent Application Publication Nos. 2015/0218236; 2016/0229913; 2017/0088603; 2017/0081406; 2017/0029505; 2010/0143353; 2010/0239633; and 2013/0156765, as well as International PCT Publication Nos. WO 2016/009232; WO 2015/132364; WO 2015/132365; WO 2015/158867; WO 2016/139365; WO 2017/005767; WO 2017/013203; WO 2017/036905; WO 2015/168643; and WO 2017/151971, and may include IVIG therapeutics, including IVIG and multimer IVIG fractions. While the structural language used to define of each of the Fc therapeutics varies slightly, each of the multi-Fc therapeutics for use in accordance with the methods of the present invention comprises at least two Fc domains that allow for binding to two or more Fc receptors or complement components. At a minimum, the Fc domain is a dimeric polypeptide (or a dimeric region of a larger polypeptide) that comprises two peptide chains or arms that associate to form a functional dimer capable of binding Fc receptors or complement components. In some embodiments, each Fc domain further comprises a multimerization domain. In such embodiments, said multimerization domain is also a dimeric polypeptide comprising two peptide chains or arms that associate to form a functional multimerization domain capable of facilitating the assembly of the dimers into a multimeric polypeptide. Therefore, the functional form of the individual fragments and domains discussed herein generally exist in a dimeric form. The monomers of the individual fragments and domains discussed herein are the single chains or arms that must associate with a second chain or arm to form a functional dimeric structure. The nature of association between the single chains or arms (e.g., cysteine bonds or electrostatic interactions) is not critical, as long as it allows for the formation of a functional Fc domain or multimerization domain.

By "directly linked" is meant two sequences connected to each other without intervening or extraneous sequences, for example, amino acid sequences derived from insertion of restriction enzyme recognition sites in the DNA or cloning fragments. One of ordinary skill in the art will understand that "directly linked" encompasses the addition or removal of amino acids so long as the multimerization capacity is substantially unaffected.

By "homologous" is meant identity over the entire sequence of a given nucleic acid or amino acid sequence. For example, by "80% homologous" is meant that a given sequence shares about 80% identity with the claimed sequence and can include insertions, deletions, substitutions, and frame shifts. One of ordinary skill in the art will understand that sequence alignments can be done to take into account insertions and deletions to determine identity over the entire length of a sequence.

It has been described that IVIG binds to and fully saturates the neonatal Fc receptor (FcRn) and that such competitive inhibition of FcRn may play an important role in the biological activity of IVIG (e.g. F. Jin et al., Human Immunology, 2005, 66(4)403-410). Since immunoglobulins that bind strongly to Fcγ receptors also bind at least to some degree to FcRn, a skilled artisan will recognize that multi-Fc therapeutics capable of binding to more than one Fcγ receptor will also bind to and may fully saturate the FcRn.

There are two human polymorphs of IgG1, termed DEL and EEM polymorphs. The DEL polymorph has a D at position 356 and an L at position 358; the EEM polymorph has an E at position 356 and an M at position 358 (Kabat numbering, SEQ ID NOs: 2 and 3, EEM and DEL polymorphs, respectively). The multi-Fc therapeutics described herein may comprise either the DEL or the EEM IgG1 polymorph. Thus, even if a sentence for a particular mutant is explicitly produced in the context of the DEL polymorphism, one of skill in the art will understand that the same mutations may be made to the EEM polymorph to yield the same results.

Fc Fragments and Domains
Fc Fragment

"Fc fragment" is a term of art that is used to describe the protein region or protein folded structure that is routinely found at the carboxy terminus of immunoglobulins. The Fc fragment can be isolated from the Fab fragment of a monoclonal antibody through the use of enzymatic digestion, for example papain digestion, which is an incomplete and imperfect process (See Mihaesco C et al., Journal of Experimental Medicine, Vol 127, 431-453 (1968)). In conjunction with the Fab fragment (containing the antigen binding domain) the Fc fragment constitutes the holo-antibody, meaning here the complete antibody. The Fc fragment consists of the carboxy terminal portions of the antibody heavy chains. Each of the chains in an Fc fragment is between about 220-265 amino acids in length and the chains are often linked via a disulfide bond. The Fc fragment often contains one or more independent structural folds or functional subdomains. In particular, the Fc fragment encompasses an Fc domain, defined herein as the minimum structure that binds an Fc receptor. An isolated Fc fragment is comprised of two Fc fragment monomers (e.g., the two carboxy terminal portions of the antibody heavy chains; further defined herein) that are dimerized. When two Fc fragment monomers associate, the resulting Fc fragment has complement and/or Fc receptor binding activity.

Fc Partial Fragment

An "Fc partial fragment" is a domain comprising less than the entire Fc fragment of an antibody, yet which retains sufficient structure to have the same activity as the Fc fragment, including Fc receptor binding activity and/or complement binding activity. An Fc partial fragment may therefore lack part or all of a hinge region, part or all of a CH2 domain, part or all of a CH3 domain, and/or part or all of a CH4 domain, depending on the isotype of the antibody from which the Fc partial domain is derived. Another example of an Fc partial fragment includes a molecule comprising the CH2 and CH3 domains of IgG1. In this example, the Fc partial fragment lacks the hinge domain present in IgG1. Fc partial fragments are comprised of two Fc partial fragment monomers. As further defined herein, when two such Fc partial fragment monomers associate, the resulting Fc partial fragment has Fc receptor binding activity and/or complement binding activity.

Fc Domain

As used herein, "Fc domain" describes the minimum region (in the context of a larger polypeptide) or smallest protein folded structure (in the context of an isolated protein) that can bind to or be bound by an Fc receptor (FcR). In both an Fc fragment and an Fc partial fragment, the Fc domain is the minimum binding region that allows binding of the molecule to an Fc receptor. While an Fc domain can be limited to a discrete homodimeric polypeptide that is bound by an Fc receptor, it will also be clear that an Fc domain can be a part or all of an Fc fragment, as well as part or all of an Fc partial fragment. When the term "Fc domains" is used in this invention it will be recognized by a skilled artisan as meaning more than one Fc domain. An Fc domain is comprised of two Fc domain monomers. As further defined herein, when two such Fc domain monomers associate, the resulting Fc domain has Fc receptor binding activity and/or complement binding activity. Thus an Fc domain is a dimeric structure that can bind complement and/or an Fc receptor.

Fc Partial Domain

As used herein, "Fc partial domain" describes a portion of an Fc domain. Fc partial domains include the individual heavy chain constant region domains (e.g., CH1, CH2, CH3 and CH4 domains) and hinge regions of the different immunoglobulin classes and subclasses. Thus, human Fc partial domains of the present invention include the CH1 domain of IgG1, the CH2 domain of IgG1, the CH3 domain of IgG1, and the hinge regions of IgG1 and IgG2. The corresponding Fc partial domains in other species will depend on the immunoglobulins present in that species and the naming thereof. Preferably, the Fc partial domains of the current invention include CH1, CH2 and hinge domains of IgG1 and the hinge domain of IgG2. The Fc partial domain of the present invention may further comprise a combination of more than one of these domains and hinges. However, the individual Fc partial domains of the present invention and combinations thereof lack the ability to bind an FcR. Therefore, the Fc partial domains and combinations thereof comprise less than an Fc domain. Fc partial domains may be linked together to form a peptide that has complement and/or Fc receptor binding activity, thus forming an Fc domain. In the present invention, Fc partial domains are used with Fc domains as the building blocks to create the multi-Fc therapeutics used in accordance with the methods of the present invention, as described herein. Each Fc partial domain is comprised of two Fc partial domain monomers. When two such Fc partial domain monomers associate, an Fc partial domain is formed.

As indicated above, each of Fc fragments, Fc partial fragments, Fc domains and Fc partial domains are dimeric proteins or domains. Thus, each of these molecules is comprised of two monomers that associate to form the dimeric protein or domain. While the characteristics and activity of the homodimeric forms was discussed above the monomeric peptides are discussed as follows.

Fc Fragment Monomer

As used herein, an "Fc fragment monomer" is a single chain protein that, when associated with another Fc fragment monomer, comprises an Fc fragment. The Fc fragment monomer is thus the carboxy-terminal portion of one of the antibody heavy chains that make up the Fc fragment of a holo-antibody (e.g., the contiguous portion of the heavy chain that includes the hinge region, CH2 domain and CH3 domain of IgG). In one embodiment, the Fc fragment monomer comprises, at a minimum, one chain of a hinge region (a hinge monomer), one chain of a CH2 domain (a CH2 domain monomer) and one chain of a CH3 domain (a CH3 domain monomer), contiguously linked to form a peptide. In one embodiment, the CH2, CH3 and hinge domains are from different isotypes. In a particular embodiment, the Fc fragment monomer contains an IgG2 hinge domain and IgG1 CH2 and CH3 domains.

Fc Domain Monomers

As used herein, "Fc domain monomer" describes the single chain protein that, when associated with another Fc domain monomer, comprises an Fc domain that can bind to complement and/or canonical Fc receptors. The association of two Fc domain monomers creates one Fc domain.

In one embodiment, the Fc domain monomer comprises, from amino to carboxy-terminus, an Fc domain comprising an IgG1 hinge, IgG1 CH2, and IgG1 CH3 and an IgG2 hinge.

Multi-Fc therapeutics

The methods of the present invention provide for determining a subject's response to any multi-Fc domain-containing compound wherein the Fc retain functionality. In a particular embodiment, the methods of the current invention are used to determine whether a subject has an adequate response to a multi-Fc therapeutic such as GL-2045, G994, G998 or another stradomer described in US Patent Application Publication Nos. 2010/0239633 or 2013/0156765, International PCT Publication No. WO 2017/019565, and International PCT Application No. PCT/US2017/043538, the contents of each of which are incorporated by reference herein in their entireties. Further, additional multi-Fc therapeutics have been described (See US Patent Application Publication Nos. 2015/0218236; 2016/0229913; 2010/0143353; 2017/0088603; 2017/0081406; and 2017/0029505, and International PCT Publication Nos. WO 2015/132364; WO 2015/132365; WO 2015/158867; WO 2015/168643; WO 2016/009232; WO 2016/139365; WO 2017/005767; WO 2017/013203; WO 2017/036905; and WO 2017/151971, each of which is incorporated by reference).

While these descriptions differ slightly in the language used to describe individual components, these multi-Fc therapeutics are substantially structurally and/or functionally similar to the stradomers described above and disclosed in US Patent Application Publication Nos. 2010/0239633 and 2013/0156765. Each essentially describes polypeptides comprised of dimeric polypeptides comprising serially linked Fc domain monomers associated to form at least two functional Fc domains (e.g. stradomer units). The linker connecting the Fc domain monomers may be a covalent bond (e.g., a peptide bond), peptide linkers, or non-peptides linkers. Further, the nature of association between Fc domain monomers to form functional Fc domains is not critical so long as it allows the formation of a functional Fc domain capable of binding canonical Fc receptors and/or complement components (e.g., cysteine bonds or electrostatic interactions).

Stradomers

In some embodiments, the multi-Fc therapeutic is a stradomer (e.g. GL-2045). US Patent Application Publication No. 2010/0239633 discloses using linked immunoglobulin Fc domains to create orderly multimerized immunoglobulin Fc biomimetics of IVIG (biologically active ordered multimers known as stradomers), which include short sequences including restriction sites and affinity tags between individual components of the stradomer for the treatment of pathological conditions including autoimmune diseases and other inflammatory conditions. See US 2010/0239633, incorporated by reference in its entirety. US Patent Application Publication No. 2013/0156765 discloses stradomers wherein the individual components are directly linked, rather than separated by restriction sites or affinity tags. US 2013/0156765 also specifically discloses a multimerizing stradomer (GL-2045) comprising an IgG1 Fc domain with an IgG2 hinge multimerization domain directly linked to its C-terminus, which exhibits enhanced multimerization relative to the N-terminal linked compound (GL-2019, described in US 2010/0239633). See US 2013/0156765, incorporated by reference in its entirety. The structure of GL-2045 is: IgG1 Hinge—IgG1CH2 IgG1 CH3-IgG2 Hinge and GL-2045 is provided as SEQ ID NO: 4 and 5 (EEM and DEL polymorphs, respectively).

The stradomers for use in the methods of the present invention are biomimetic compounds capable of binding complement and/or canonical Fc receptors. In addition, one of skill in the art will understand that any conformation of a stradomer (e.g., serial, cluster, core, or Fc fragment) can be used in accordance with the methods described herein. Serial stradomers are dimeric peptides comprised of at least two serially linked Fc domains. Serial stradomers are thus capable of binding two or more Fc receptors.

Cluster stradomers are stradomers with a radial form and having a central moiety "head" that multimerizes and two or more "legs", wherein each leg comprises one or more Fc domains capable of bind at least one Fc receptors and/or complement. Cluster stradomers are also referred to as "multimerizing stradomers" (e.g., GL-2045). As will be evident, the Fc fragments, Fc partial fragments, Fc domains and Fc partial domains discussed above are used in the construction of the various stradomer conformations. Further, it is the individual Fc domain monomers and Fc partial domain monomers, also discussed above, that are first produced to form dimeric stradomer units, and that then multimerize through the inclusion of a multimerization domain (e.g. an IgG2 hinge) to form the multimeric structures that are the cluster stradomers of the present invention. Specific stradomers are described in great detail in US 2010/0239633 and US 2013/0156765, the contents of both of which are herein incorporated by reference in their entireties.

Core stradomers comprise a core moiety to which two or more polypeptides comprising one or more Fc domains are bound, thereby creating a biomimetic compound capable of binding two or more Fcγ receptors. An Fc fragment, Fc partial fragment, serial stradomer, or cluster stradomer unit can each independently serve as one or both (if they comprise two Fc domains) of the core stradomer units in a core stradomer because each of these molecules contains at least one Fc domain. In some embodiments, the core moiety is a polystyrene bead. In some embodiments, each of the Fc domains further comprise an IgM CH4 domain and the core moiety comprises a J-chain resulting a biomimetic capable of binding multiple Fcγ receptors.

One of skill in the art will understand that stradomers do not comprise antigen binding Fab fragments. Such Fab-bearing compounds are generally referred to as "stradobodies." Thus, in one aspect, the multi-Fc therapeutics useful in accordance with the present invention specifically lack an antigen-binding Fab domain.

In some embodiments, the dimeric polypeptides comprise multimerization domains that facilitate the assembly of the dimeric polypeptides into multimeric proteins. As used herein, "multimerization domain" refers to a domain that facilitates the assembly of the polypeptides comprising Fc domains into a multimeric Fc protein. The nature of the multimerization domain is not critical, so long as it allows for assembly of the dimeric polypeptides into a multi-Fc protein capable of presently polyvalent Fc to Fc receptors and/or complement components (e.g., a multi-Fc therapeutic). In some embodiments, the multimerization domain is an IgG2 hinge. In some embodiments, the dimeric polypeptides comprise terminal IgM CH4 domains. In some embodiments, inclusion of such domains allows for the self-aggregation of the stradomers with a core moiety, such as a J-chain, to form a core stradomer.

Complement-preferential Stradomers, General Stradomers, and Hexameric Stradomers International PCT Publication No. WO 2017/0195656 describes complement-preferential, multi-Fc therapeutics comprising stradomers, and International PCT Application No. PCT/US2017/043538 describes general and hexameric multi-Fc therapeutics comprising stradomers, the basic structures of which are described above. These stradomers comprise multimerization domains and further comprise point mutations in the CH1 and/or CH2 regions of the Fc domains. The particular point mutations enable the complement-preferential stradomers to preferentially bind one or more complement components, such as C1q, compared to normal non-aggregated human immunoglobulin Fc (WO 2017/0195656). This preferential binding is achieved directly through increased binding to complement components, or indirectly through decreased binding of the stradomers to canonical Fc receptors. As such, these compounds comprise stradomer units capable of multimerizing into a multi-Fc therapeutic and further capable of preferential binding to complement components. Similarly, the particular combination of point mutations present in the general stradomers enable binding to complement components and/or Fc receptors with an increased or decreased affinity depending on the specific combination of mutations, and enable the hexameric stradomers to preferentially form multimerized Fc therapeutics comprising six Fc domains (PCT/US2017/043538).

Selective Immunomodulator of Fc Receptors (SIF)

US Patent Application Publication No. 2016/0229913 describes selective immunomodulators of Fc receptors (SIFs) including a first polypeptide comprising; a first Fc domain monomer, a linker, and a second Fc domain monomer; a second polypeptide comprising a third Fc domain monomer; and a third polypeptide comprising a fourth Fc domain monomers. Said first and third Fc domain monomers combine to form a first Fc domain, and said second and fourth Fc domain monomers combine to form a second Fc domain monomer. These compounds thus form two functional Fc domains through the association of three independent polypeptides (SIF3™). Additional embodiments disclosed in US 2016/0229913 describe the formation of compounds comprising up to 5 Fc domain monomers. These compounds essentially comprise serially linked Fc domains (See US Patent Application Publication Nos. 2005/0249723 and 2010/0239633) and individual Fc domain monomers (variants of which are disclosed in US Patent Application Publication No. 2006/0074225) that assemble through sequence mutations. As such, the end result is a multi-Fc therapeutic akin to a serial stradomer. The SIF3™ compounds described in US 2016/0229913 do not comprise a multimerization domain. Additional SIF embodiments are described in International PCT Publication No. WO 2017/151971.

Tailpiece Fc Multimers

US Patent Application Publication No. 2015/0218236 discloses a method of treatment for an autoimmune or inflammatory disease comprising administering a multi-Fc therapeutic to a patient in need thereof. The multi-Fc therapeutic described therein comprises 5, 6, or 7 polypeptide monomer units wherein each monomer unit comprises an Fc receptor binding portion comprising two IgG heavy chain constant regions. Each IgG heavy chain constant region comprises a cysteine residue linked via a disulfide bond to a cysteine residue of an IgG heavy chain constant region of an adjacent polypeptide monomer. As the peptide "monomers" described in US 2015/0218236 are comprised of two IgG heavy chains, they are actually dimeric proteins (e.g., Fc domains). In some embodiments of US 2015/0218236, the monomer units further comprise a tailpiece region that facilitates the assembly of the monomer units into a polymer (e.g., a multimer). As such, a "tailpiece" as used therein is functionally equivalent to the multimerization domains described in the instant specification and in US 2010/0239633 and US 2013/0156765. This compound essentially comprises stradomer units with multimerization domains that assemble to form a cluster stradomer, as described above. Additional tailpiece Fc multimers are described in International PCT Publication Nos. WO 2016/009232 and WO 2017/005767.

Fc Multimers Comprising Mutations at Position 309

International PCT Publication Nos. WO 2015/132364, WO 2015/132365, WO 2015/158867, WO 2017/036905, WO 2017/013203, and WO 2016/139365, and US Patent Application Publication Nos. 2017/0081406, 2017/0088603, and 2017/0029505 describe a multi-Fc therapeutic comprised of polypeptide monomer units, wherein each polypeptide monomer comprises an Fc domain. Each of said Fc domains are comprised of two heavy chain Fc-regions each of which comprises a cysteine at position 309 (WO 2015/132365 and WO 2016/139365) or an amino acid other than cysteine at position 309 (WO 2015/132364, WO 2017/036905, and WO 2017/013203). As such the polypeptide "monomers" described in International PCT Publication Nos. WO 2015/132364, WO 2015/132365, WO 2015/158867, WO 2017/036905, WO 2017/013203, and WO 2016/139365, and US Patent Application Publication Nos. 2017/0081406, 2017/0088603, and 2017/0029505 are actually dimeric proteins (e.g., Fc domain monomers as used herein). Each of the heavy chain Fc-regions is fused to a tailpiece at its C-terminus that causes the monomer to assemble into a multimer. As such, a "tailpiece" as used therein is functionally equivalent to the multimerization domains described in the instant specification. In a preferred embodiment therein, the multi-Fc therapeutic is a trimeric or hexameric multimer. This compound essentially comprises stradomer units with multimerization domains that assemble to form a cluster stradomer, as described above.

Fc Multimers Comprised of Serially-Linked Fc Domain Monomers

US Patent Application Publication No. 2010/0143353 describes a multi-Fc therapeutic comprising at least a first and second Fc fragment of IgG, at least one of the first IgG fragments of IgG comprising at least one CH2 domain and a hinge region, and wherein the first and second Fc fragments of IgG are bound through the hinge to form a chain. In some embodiments of US 2010/0143353, substantially similar chains associate to form a dimer. In other embodiments of US 2010/0143353, multiple substantially similar chains associate to form a multimer. As described herein, an Fc fragment encompasses an Fc domain. As such, the therapeutics disclosed in US 2010/0143353 comprise a multimerizing Fc therapeutic capable of binding at least two Fc receptors and assembling into a multimer.

Methods of Treatment

The methods of the current invention further provide for methods of treating autoimmune and inflammatory diseases comprising administering at least one cumulative escalated dose of a multi-Fc therapeutic to a patient, wherein the patient has been determined to have an inadequate response to a previously administered of the multi-Fc therapeutic.

In some embodiments, an "inadequate response" to a multi-Fc therapeutic refers to blood levels of iC3b lower than a predetermined threshold following administration of a previously administered dose of the multi-Fc therapeutic. In some embodiments, an "inadequate response" to a multi-Fc therapeutic refers to a change in blood levels of iC3b of less than about 10% of baseline following administration of a previously administered dose of the multi-Fc therapeutic. In some embodiments, an "inadequate response" to a multi-Fc therapeutic refers to a change in blood levels of iC3b of less than about 25%, or less than about 50% of baseline following administration of a previously administered dose of the multi-Fc therapeutic. In some embodiments, an "inadequate response" to a multi-Fc therapeutic refers to a change in blood levels of iC3b that remains within normal values as established for the patient and/or patient population. In some embodiments, an "inadequate response" to a multi-Fc therapeutic refers to an increase in blood levels of iC3b that is less than 10%, less than 25%, or less than 50% increase over a baseline iC3b measurement following administration of a previously administered dose of the multi-Fc therapeutic. In some embodiments, an "inadequate response" to a multi-Fc therapeutic refers to a change in blood levels of iC3b that remains within about 150% of normal values as established for the population.

In some embodiments, previously administered dose of the multi-Fc therapeutic is known to be unable to result in an adequate response to the multi-Fc therapeutic is administered to a subject. In such embodiments, the administration of the multi-Fc at a dose that is unable to elicit an adequate response may be administered in order to assess any potential off-target effects of the multi-Fc therapeutic, such as an allergic reaction or other aberrant immune reaction not typically observed in subjects. Escalating doses of the multi-Fc therapeutic may then be subsequently administered.

Patients determined to have an inadequate response to a previously administered dose of a multi-Fc therapeutic may be treated with a "cumulative escalated dose" wherein the "cumulative escalated dose" is comprised of either an "escalated dose" or an escalated dose and one or more "incremental doses." As used herein, a "previously administered dose" refers to the dose of a multi-Fc therapeutic that was administered to a patient in the preceding dosing period. In some embodiments, the previously administered dose refers to a cumulative escalated dose. In some embodiments, the previously administered dose refers to a starting dose. As used herein, a "starting dose" refers to the lowest commonly used dose of said multi-Fc therapeutic. In some embodiments, the starting dose may be the lowest commercially approved dose of the multi-Fc therapeutic for a given disease or disorder. As used herein "lowest commercially approved dose" refers to the lowest dose of a given multi-Fc therapeutic that is approved for the treatment of an indicated disease or disorder. However, the medical standard of care for a given disease or disorder may require beginning treatment with a lower dose of the multi-Fc therapeutic than the lowest commercially approved dose. In such embodiments, the starting dose may be 90%, 80%, 70%, 60%, 50%, or less of the lowest commercially approved dose or of the medical standard of care dose, if lower. Alternatively, the medical standard of care for a given disease or disorder may require beginning treatment with a higher dose of a multi-Fc therapeutic. In such embodiments, the starting dose may be 105%, 110%, 125%, 150%, 200%, 250%, or more of the lowest commercially approved dose. For example, the lowest commercially approved dose of IVIG may be 600 mg/Kg for treating immunodeficiency diseases but medical standard of care treatment of an autoimmune condition, such as CIDP, may be 2000 mg/Kg. Where a lowest commercially approved dose has not been defined, a starting dose may also refer to the initial dose recommended by the manufacturer and/or physician or the initial dose that has been subsequently described in the scientific literature. Thus, in one embodiment, the starting dose is the actual first dose given to the particular patient being treated with a multi-Fc therapeutic or IVIG.

In one embodiment, a method for treating an inflammatory disease in a patient determined to have an inadequate response to a previously administered dose of a multi-Fc therapeutic is provided, comprising administering to the patient one or more escalated doses. As used herein, an "escalated dose" is a dose of a multi-Fc therapeutic that is either higher in amount than the previously administered dose of a multi-Fc therapeutic or is given more frequently than anticipated. Such one or more escalated doses are in total a "cumulative escalated dose" of the multi-Fc therapeutic. As used herein, a "cumulative escalated dose" is a dose of a multi-Fc therapeutic administered during a dosing period that is cumulatively greater than the previously administered dose of a given multi-Fc therapeutic. In some embodiments, the cumulative escalated dose is about 105%, 110%, 115%, 120%, 125%, 150%, 200%, or more than the previously administered dose. In some embodiments, a cumulative escalated dose comprises an escalated dose that is administered throughout a dosing period, wherein the escalated dose is greater than the dose of a multi-Fc therapeutic administered during a preceding dosing period. In some embodiments, the escalated dose is about 105%, 110%, 115%, 120%, 125%, 150%, or 200% or more than the dose of a multi-Fc therapeutic administered during a preceding dosing period. In some embodiments, a cumulative escalated dose comprises an escalated dose that is equal in amount to and is administered more frequently than a dose of a multi-Fc therapeutic during a preceding dosing period. In some embodiments, the escalated dose is administered at least once more than the previously administered dose of a multi-Fc therapeutic during a given dosing period. In some embodiments, the escalated dose is administered at least 2, 3, 4, 5, 10, 15, 20, or more times than the previously administered dose of a multi-Fc therapeutic during a given dosing period.

At any point throughout a dosing period, blood levels of iC3b can be measured and the dose of the multi-Fc administered during said dosing period adjusted accordingly. In such embodiments, the cumulative escalated dose may comprise an escalated dose administered for a portion of a dosing period followed by an "incremental dose" administered for the remainder of the dosing period. As used herein, an "incremental dose" is a dose of a multi-Fc therapeutic that is greater in amount than an escalated dose and is administered within the same dosing period as the escalated dose. In some embodiments, an incremental dose is an increased dose given within a single dosing period that is given after the escalated dose and that is higher than the escalated dose. In some embodiments, an incremental dose is a dose given within a single dosing period and is administered more frequently than the previously anticipated dosing schedule for the escalated dose. In some embodiments, an incremental dose is about 105%, 110%, 115%, 120%, 125%, 150%, or 200% or more than the escalated dose administered during the same dosing period. As such, in some embodiments a cumulative escalated dose may comprise an escalated dose and one or more incremental doses administered during the same dosing period. A schematic of exemplary dosing schemes is provided in FIG. 8.

By way of further example, the recommended initial dose for subcutaneous administration of liquid Gammagard™ (human immunoglobulin infusion produced by Baxalta) for an adult male is 400 mg/kg every four weeks. In this example, the starting dose of Gammagard™ would be 400 mg/kg. If it is determined by the methods described herein that the patient has an inadequate response to the initial dose of the multi-Fc therapeutic, a cumulative escalated dose is administered. In this clarifying example, the cumulative escalated dose may comprise an escalated dose, for example 500 mg/Kg, administered for the duration of the dosing period. Alternatively, the cumulative escalated dose may comprise an escalated dose, wherein the escalated dose is equal in amount to the starting dose (e.g., 400 mg/mL) and is administered more frequently than the starting dose (e.g., at least once more than the starting dose). Alternatively, the cumulative escalated dose may comprise either of these escalated doses of administered for a portion of the dosing period and an incremental dose (e.g., 550 mg/Kg) administered for the remainder of the dosing period.

As used herein a "dosing period" refers to the period of time over which a multi-Fc therapeutic is administered. A dosing period may be at least 1 day, 2 days, 3 days, 4 days, 1 week, 1 month, 6 months, or longer. In some embodiments, the multi-Fc therapeutic may be administered at least one, two, three, four, five, six, seven, or more times during a dosing period. As a clarifying example, a dosing period may be 6 months, wherein a multi-Fc therapeutic is administered once every month, for a total of 6 administrations. The methods described herein may comprise administering a multi-Fc therapeutic for at least 1, 2, 3, 4, 5, 10, 15, or more dosing periods.

Figure 8:
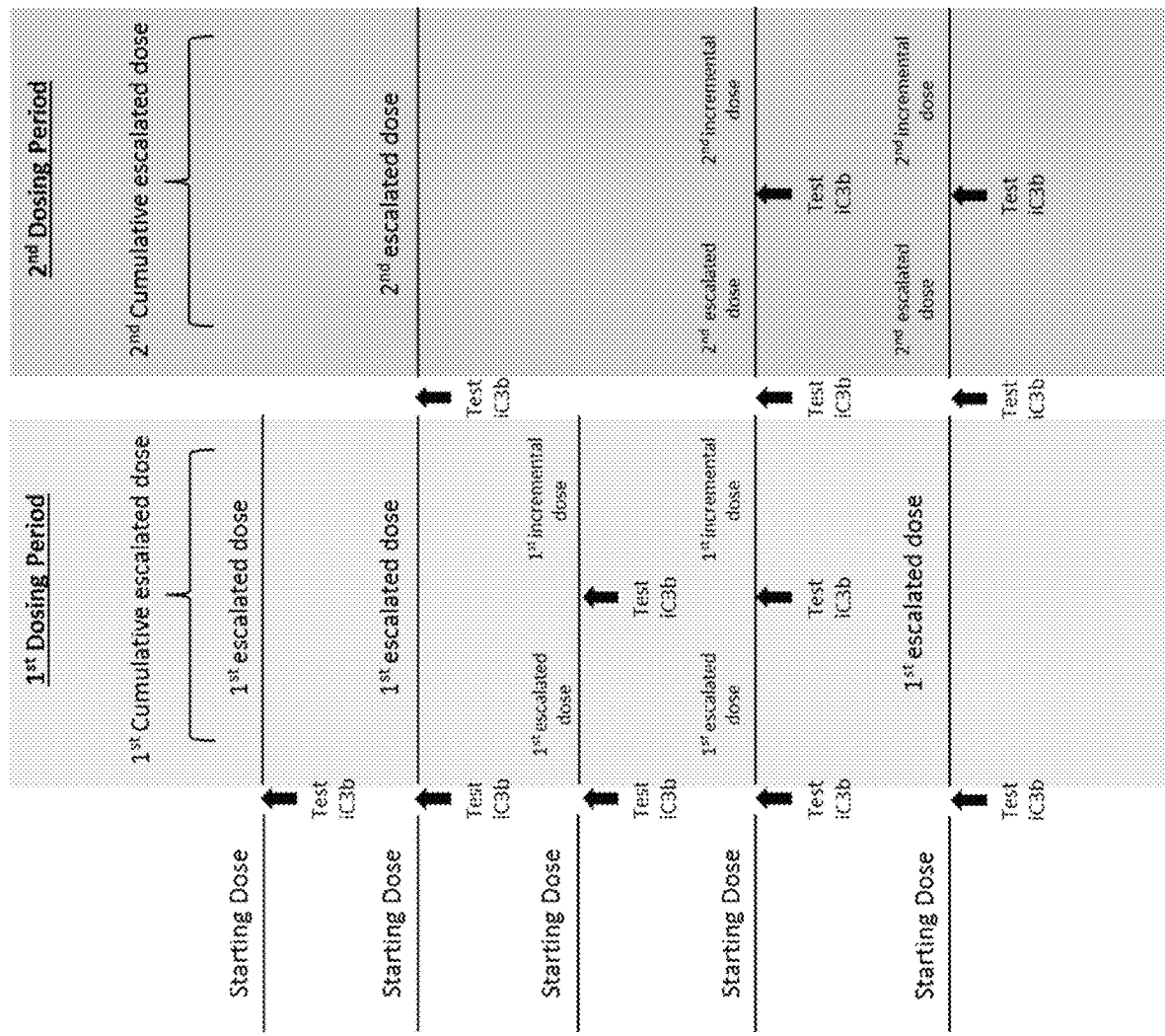
FIG. 8 illustrates potential embodiments for iC3b testing and dosing of multi-Fc therapeutics.

The doses of multi-Fc therapeutics defined herein (e.g., escalated doses and incremental doses) may be combined in a number of ways over a number of dosing periods for use according to the methods described herein. The relationship between escalated doses, incremental doses, cumulative escalated doses, and dosing periods is illustrated in FIG. 8. The embodiments disclosed in FIG. 8 are for illustrative purposes only and are in no way limiting of the methods described herein.

In some embodiments, an inadequate response to a multi-Fc therapeutic is determined by measuring circulating levels of iC3b, or a surrogate iC3b marker, in a patient. In some embodiments, a level of iC3b that is lower than a predetermined threshold is indicative of an inadequate response to a multi-Fc therapeutic. In such embodiments, an escalated dose of the multi-Fc therapeutic may be administered. In some embodiments, a level of iC3b that is higher than a predetermined threshold is indicative of an adequate response to a multi-Fc therapeutic. In such embodiments, an escalated dose of the multi-Fc therapeutic may not be administered. In some embodiments, the predetermined threshold of iC3b is about 25 µg/mL to about 300 µg/mL above assay background. In some embodiments, the predetermined threshold of iC3b is about 50 µg/mL to about 200 µg/mL above assay background. In some embodiments, the predetermined threshold of iC3b is about 75 µg/mL to about 125 µg/mL above assay background. In some embodiments, the predetermined threshold of iC3b is about 100 µg/mL above assay background. In some embodiments, a change in iC3b levels of less than 10% from a patient's baseline level is indicative of an inadequate response to a multi-Fc therapeutic. In some embodiments, a change in iC3b levels of less than 10% from a patient's previously determined iC3b level is indicative of an inadequate response to a multi-Fc therapeutic. In some embodiments, a change in iC3b levels of less than 20%, less than 25%, less than 30%, less than 35%, less than 40%, or less than 50% is indicative of an inadequate response to a multi-Fc therapeutic.

In further embodiments, a change in the levels of a surrogate marker for iC3b (e.g., C4a, C4a desArg, C3a, C3a desArg, C3f, C3c, C3dg, C3d, and/or C3g) of less than 10% from a patient's baseline level is indicative of an inadequate response to a multi-Fc therapeutic. In some embodiments, a change in the levels of a surrogate marker for iC3b of less than 10% from a patient's previously determined iC3b level is indicative of an inadequate response to a multi-Fc therapeutic. In some embodiments, a change in the levels of a surrogate marker for iC3b of less than 20%, less than 25%, less than 30%, less than 35%, less than 40%, or less than 50% is indicative of an inadequate response to a multi-Fc therapeutic. In some embodiments, an increase in the levels of a surrogate marker for iC3b (e.g., C4a, C4a desArg, C3a, C3a desArg, C3f, C3c, C3dg, C3d, and/or C3g) of less than 10% from a patient's baseline level or from a patient's previously determined iC3b level is indicative of an inadequate response to a multi-Fc therapeutic. In some embodiments, an increase in the levels of a surrogate marker for iC3b of less than 20%, less than 25%, less than 30%, less than 35%, less than 40%, or less than 50% from a patient's baseline level or from a patient's previously determined iC3b level is indicative of an inadequate response to a multi-Fc therapeutic. In some embodiments, a level of a surrogate marker for iC3b that is lower than a predetermined threshold is indicative of an inadequate response to a multi-Fc therapeutic. In some embodiments, the predetermined threshold for a surrogate marker of iC3b is about 5 ng/mL to about 30 ng/mL. In some embodiments, the predetermined threshold for a surrogate marker of iC3b is about 10 ng/mL to about 20 ng/mL.

The terms "determining," "measuring," and "quantifying" as used herein in reference to iC3b levels refer to the assessment of blood levels of iC3b by an iC3b assay at a particular point in time. The time point at which iC3b generation is assessed may be prior to dosing, less than 5 minutes, 15 minutes, 30 minutes, 1 hour, 2 hours, 4 hours, 12 hours, 24 hours, 2 days, 3 days, 7 days, 14 days, 1 month or more after use of a multi-Fc therapeutic in an appropriate patient. As described above, in some embodiments, levels of upstream complement cleavage products (e.g., C3a, C3a desArg, C4a and/or C4a desArg) or levels of iC3b cleavage and/or degradation products (e.g., iC3b1, iC3b2, C3f, C3dg, C3d, and/or C3g) are used as surrogates for downstream iC3b levels. The methods described herein for determining a level of circulating iC3b in a patient apply equally to determining levels of iC3b1, iC3b2, C4a, C4a desArg, C3a, C3a desArg, C3f, C3dg, C3d, and/or C3g, although the skilled artisan will recognize that the ideal timing of such measurements may differ from iC3b. Levels of iC3b1, iC3b2, C4a, C4a desArg, C3a, C3a desArg, C3f, C3dg, C3d, and/or C3g may be determined by ELISA, western blot, and/or flow cytometry or other similar methods. The terms "blood levels of iC3b" and "iC3b levels" are used interchangeably herein and refer to the circulating levels of iC3b in a patient or subject at a given time.

Assays for determining inhibition of CDC are known in the art and may be accomplished in a variety of ways using tumor cell lines, fresh red blood cells, or other materials. An antibody against a target antigen and complement C1q are generally necessary in these assays in order to activate the complement pathway leading to CDC of the target cell in the assay.

In some embodiments, the level of circulating iC3b is determined by an immunoassay, such as an enzyme-linked immunosorbent assay (ELISA) or western blot. In some embodiments, levels of circulating iC3b are determined by the immunoassay methods described in U.S. Pat. No. 9,164,088. Such assays are capable of detecting soluble iC3b. As such, the predetermined threshold of iC3b may be based on a concentration of iC3b determined from a blood sample. In some embodiments, iC3b may be bound to the surface of a circulating cell. In such embodiments, the level of circulating iC3b may be determined by flow cytometry. In such embodiments, the predetermined threshold of circulating iC3b may be represented as a fraction or percentage of cells that are iC3b$^+$ and/or as a fraction or percentage of cells with given a relative Mean Fluorescent Intensity (MFI) for iC3b. In some embodiments, the predetermined threshold of iC3b is 25% of neutrophils and monocytes that are iC3b+. In further embodiments, the predetermined threshold of iC3b is an iC3b MFI of 125% of the baseline iC3b MFI. In some embodiments, the iC3b level is determined by an immunoassay. Methods of determining soluble and cell-bound iC3b may be combined in order to generate a predetermined threshold value (e.g., a concentration of iC3b lower than 0.02 μg/mL and/or a percentage of iC3b+ monocytes and neutrophils less than 25% and/or an iC3b MFI on monocytes and neutrophils that is less than 125% of baseline). In further embodiments, the immunoassay is an ELISA or a western blot. In some embodiments, the iC3b level is determined by flow cytometry.

Additional methods to determine the effective dose of a multi-Fc therapeutic are provided herein, comprising administering a multi-Fc therapeutic to a subject in need thereof at a starting dose, measuring circulating levels of iC3b, determining that the subject requires a cumulative escalated dose of the multi-Fc therapeutic if the circulating level of iC3b in the subject is below a predetermined threshold or if the circulating levels of iC3b blood levels have an inadequate change from pre-administration baseline following administration of the starting dose of the multi-Fc therapeutic, and administering a cumulative escalated dose of the multi-Fc therapeutic if needed. In further embodiments, the process of determining circulating levels of iC3b is repeated after administration of the cumulative escalated dose. If the circulating levels of iC3b remain below a predetermined threshold after the administration of a cumulative escalated dose for a first dosing period or if the circulating levels of iC3b blood levels have an inadequate change from pre-administration baseline, a second cumulative escalated dose is administered for a second dosing period. In such embodiments, the second cumulative escalated dose is a higher dose than the first cumulative escalated dose. In such embodiments, the second dosing period may be a shorter, longer, or the same amount of time as the first dosing period. In still further embodiments, this process of administering increasingly higher doses of the multi-Fc therapeutic in consecutive dosing periods is repeated until a predetermined threshold of iC3b is reached, or until the circulating levels of iC3b blood levels have an adequate change from pre-administration baseline.

New technologies for measuring iC3b and/or a change or improvement in sensitivity, specificity, positive predictive value, and/or negative predictive value of an existing technology or assay does not fundamentally change this disclosure. The new and/or improved technology for assessing iC3b can be employed in the methods described herein.

One skilled in the art will appreciate that the act of administering a multi-Fc therapeutic to the patient and the act of measuring circulating levels of iC3b do not have to be performed by the same individual. Thus, in some embodiments, the act of administering a multi-Fc therapeutic to the patient and the act of measuring circulating levels of iC3b are performed by different individuals. In some embodiments, the act of administering a multi-Fc therapeutic to the patient and the act of measuring circulating levels of iC3b are performed by the same individual. Further, in some embodiments, the act of administering a multi-Fc therapeutic to the patient and the act of measuring circulating levels of iC3b are performed at different geographical locations (e.g., a multi-Fc therapeutic is administered by a physician in a clinical setting and blood is drawn from the patient and sent to an off-site laboratory for determining iC3b levels). In some embodiments, the two acts are performed at the same location and/or under the direction of a single individual or group of people.

The "effective dose" or "therapeutically effective amount" as used herein refers to an amount of a multi-Fc therapeutic that results in levels of iC3b above a predetermined threshold and that also results in an improvement or remediation of the symptoms of the disease or condition. The improvement is any improvement or remediation of the disease or condition, or symptom of the disease or condition. In some embodiments, the improvement is an observable or measurable improvement, or may be an improvement in the general feeling of well-being of the subject. Thus, one of skill in the art realizes that a treatment may improve the disease condition, but may not be a complete cure for the disease. Specifically, improvements in subjects may include one or more of: decreased inflammation; decreased inflammatory laboratory markers such as C-reactive protein; decreased autoimmunity as evidenced by one or more of improvements in autoimmune markers such as autoantibodies or in platelet count, white cell count, or red cell count, decreased rash or purpura, decrease in weakness, numbness, or tingling, increased glucose levels in patients with hyperglycemia, decreased joint pain, inflammation, swelling, or degradation, decrease in cramping and diarrhea frequency and volume, decreased angina, decreased tissue inflammation, or decrease in seizure frequency; decreases in cancer tumor burden, increased time to tumor progression, decreased cancer pain, increased survival or improvements in the quality of life; or delay of progression or improvement of osteoporosis.

As used herein, "prophylaxis" can mean complete prevention of the symptoms of a disease, a delay in onset of the symptoms of a disease, or a lessening in the severity of subsequently developed disease symptoms.

The term "subject" or "patient" as used herein, is taken to mean any mammalian subject to which a multi-Fc therapeutic is administered according to the methods described herein. In a specific embodiment, the methods of the present disclosure are employed to treat a human subject. The methods of the present disclosure may also be employed to treat non-human primates (e.g., monkeys, baboons, and chimpanzees), mice, rats, bovines, horses, cats, dogs, pigs, rabbits, goats, deer, sheep, ferrets, gerbils, guinea pigs, hamsters, bats, birds (e.g., chickens, turkeys, and ducks), fish, and reptiles. In some embodiments, the methods of the present disclosure are employed to treat a patient or subject that does not have a deficiency in Factor H and/or Factor I. In some embodiments, the methods of the present disclosure are employed to treat a patient or subject that does not have a mutation in the Factor H and/or Factor I gene that affects the function of the Factor H and/or Factor I protein. In some embodiments, the patients treated by the methods of the present disclosure does not suffer from hemolytic uremic syndrome, membranoproliferative glomerulonephritis, or age-related macular degeneration that is associated with and/or caused by a mutation or deficiency in Factor H and/or Factor I.

The route of administration will vary, naturally, with the location and nature of the disease being treated, and may include, for example intradermal, transdermal, subdermal, parenteral, nasal, intravenous, intramuscular, intranasal, subcutaneous, percutaneous, intratracheal, intraperitoneal, intratumoral, perfusion, lavage, direct injection, and oral administration.

In one embodiment, the multi-Fc therapeutic is administered intravenously, subcutaneously, orally, intraperitoneally, sublingually, buccally, transdermally, rectally, by subdermal implant, or intramuscularly. In particular embodiments, the multi-Fc therapeutic is administered intravenously, subcutaneously, or intramuscularly.

Medical conditions suitable for treatment with a multi-Fc therapeutic include allergies, cancer, autoimmune diseases, infectious diseases, inflammatory diseases, and any disease caused by or associated with complement activation or complement-mediated effector functions, including increased or inappropriate complement activity. Such medical conditions include those that are currently or have previously been treated with complement binding drugs such as eculizumab. Eculizumab binds to complement protein C5 (a complement protein that is downstream of C1 and C1q in the classical complement pathway), inhibiting its cleavage and subsequent complement-mediated cell lysis. Multi-Fc therapeutics provide a safe and effective alternative to other complement-binding drugs known in the art. For example, in some embodiments, multi-Fc therapeutics bind C1q, the first subunit in the C1 complex of the classical complement pathway. Medical conditions suitable for treatment with the methods described herein include, but are not limited to, myasthenia gravis, hemolytic uremic syndrome (HUS), atypical hemolytic uremic syndrome (aHUS), paroxysmal nocturnal hemoglobinuria (PNH), membranous nephropathy, neuromyelitis optica, antibody-mediated rejection of allografts, lupus nephritis, macular degeneration, sickle cell disease, and membranoproliferative glomerulonephritis (MPGN). Additional medical conditions suitable for treatment with multi-Fc therapeutics include those currently routinely treated with broadly immune suppressive therapies including IVIG, or in which IVIG has been found to be clinically useful such as autoimmune cytopenias, chronic inflammatory demyelinating polyneuropathy, Guillain-Barre' syndrome, myasthenia gravis, anti-Factor VIII autoimmune disease, dermatomyositis, vasculitis, and uveitis (See, F. G. van der Meche et al., N. Engl. J. Med. 326, 1123 (1992); P. Gajdos et al, Lancet, 323 (1984); Y. Sultan et al., Lancet ii, 765 (1984); M. C. Dalakas et al., N. Engl. J. Med. 329, 1993 (1993); D. R. Jayne et al, Lancet 337, 1137 (1991); P. LeHoang et al., Ocul. Immunol. Inflamm. 8, 49 (2000)) and those cancers or inflammatory disease conditions in which a monoclonal antibody may be used or is already in clinical use. Conditions included among those that may be effectively treated by the compounds that are the subject of this invention include an inflammatory disease with an imbalance in cytokine networks, an autoimmune disorder mediated by pathogenic autoantibodies or autoaggressive T cells, or an acute or chronic phase of a chronic relapsing autoimmune, inflammatory, or infectious disease or process.

In addition, other medical conditions having an inflammatory component involving complement will benefit from treatment with multi-Fc therapeutics such as amyotrophic lateral sclerosis, Huntington's disease, Alzheimer's Disease, Parkinson's Disease, myocardial infarction, stroke, hepatitis B, hepatitis C, human immunodeficiency virus-associated inflammation, adrenoleukodystrophy, and epileptic disorders especially those believed to be associated with postviral encephalitis including Rasmussen Syndrome, West Syndrome, and Lennox-Gastaut Syndrome.

Complement inhibition has been demonstrated to decrease antibody-mediated diseases (See for example Stegall et al., American Journal of Transplantation 2011 November; 11(1):2405-2413). The methods of the present invention may also be used to treat a disease or condition that is antibody-mediated. Auto-antibodies mediate many known autoimmune diseases and likely play a role in numerous other autoimmune diseases. Recognized antibody mediated diseases in which the methods of the present invention may be used include, but are not limited to, anti-glomerular basement membrane antibody mediated nephritis including Goodpasture's; anti-donor antibodies (donor-specific alloantibodies) in solid organ transplantation; anti-Aquaporin-4 antibody in neuromyelitis optica; anti-VGKC antibody in neuromyotonia, limbic encephalitis, and Morvan's syndrome; anti-nicotinic acetylcholine receptor and anti-MuSK antibodies in Myasthenia gravis; anti-VGCC antibodies in Lambert Eaton myasthenic syndrome; anti-AMPAR and anti-GABA(B)R antibodies in limbic encephalitis often associated with tumors; anti-GlyR antibodies in stiff person syndrome or hyperekplexia; anti-phospholipid, anti-cardiolipin, and anti-$\beta_2$ glycoprotein I antibodies in recurrent spontaneous abortion, Hughes syndrome, and systemic lupus erythematosus; anti-glutamic acid decarboxylase antibodies in stiff person syndrome, autoimmune cerebellar ataxia or limbic encephalitis; anti-NMDA receptor antibodies in a newly-described syndrome including both limbic and subcortical features with prominent movement disorders often in young adults and children that is often associated with ovarian teratoma but can be non-paraneoplastic; anti-double stranded DNA, anti-single stranded DNA, anti-RNA, anti-SM, and anti-C1q antibodies in systemic lupus erythematosus; anti-nuclear and anti-nucleolar antibodies in connective tissue diseases including scleroderma, Sjogren's syndrome, and polymyositis including anti-Ro, anti-La, anti-Scl 70, anti-Jo-1; anti-rheumatoid factor antibodies in rheumatoid arthritis; anti-hepatitis B surface antigen antibodies in polyarteritis nodosa; anti-centromere antibodies in CREST syndrome; anti-streptococcal antibodies in or as a risk for endocarditis; anti-thyroglobulin, anti-thyroid peroxidase, and anti-TSH receptor antibodies in Hashimoto's thyroiditis; anti-U1 RNP antibodies in mixed connective tissue disease and systemic lupus erythematosus; and anti-desmoglein and anti-keratinocyte antibodies in pemphigus.

Multi-Fc therapeutics may be used to treat conditions including but not limited to congestive heart failure (CHF), vasculitis, rosacea, acne, eczema, myocarditis and other conditions of the myocardium, systemic lupus erythematosus, diabetes, spondylopathies, synovial fibroblasts, and bone marrow stroma; bone loss; Paget's disease, osteoclastoma; multiple myeloma; breast cancer; disuse osteopenia; malnutrition, periodontal disease, Gaucher's disease, Langerhans' cell histiocytosis, spinal cord injury, acute septic arthritis, osteomalacia, Cushing's syndrome, monoostotic fibrous dysplasia, polyostotic fibrous dysplasia, periodontal reconstruction, and bone fractures; sarcoidosis; osteolytic bone cancers, lung cancer, kidney cancer and rectal cancer; bone metastasis, bone pain management, and humoral malignant hypercalcemia, ankylosing spondylitis and other spondyloarthropathies; transplantation rejection, viral infections, hematologic neoplasias and neoplastic-like conditions for example, Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplasmacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, langerhans cell histiocytosis, myeloid neoplasias such as acute myelogenous leukemias, including AML with maturation, AML without differentiation, acute promyelocytic leukemia, acute myelomonocytic leukemia, and acute monocytic leukemias, myelodysplastic syndromes, and chronic myeloproliferative disorders, including chronic myelogenous leukemia, tumors of the central nervous system, e.g., brain tumors (glioma, neuroblastoma, astrocytoma, medulloblastoma, ependymoma, and retinoblastoma), solid tumors (nasopharyngeal cancer, basal cell carcinoma, pancreatic cancer, cancer of the bile duct, Kaposi's sarcoma, testicular cancer, uterine, vaginal or cervical cancers, ovarian cancer, primary liver cancer or endometrial cancer, tumors of the vascular system (angiosarcoma and hemangiopericytoma)) or other cancer.

"Cancer" herein refers to or describes the physiological condition in mammals that is typically characterized by unregulated cell growth. Examples of cancer include but are not limited to carcinoma, lymphoma, blastoma, sarcoma (including liposarcoma, osteogenic sarcoma, angiosarcoma, endotheliosarcoma, leiomyosarcoma, chordoma, lymphangiosarcoma, lymphangioendotheliosarcoma, rhabdomyosarcoma, fibrosarcoma, myxosarcoma, and chondrosarcoma), neuroendocrine tumors, mesothelioma, synovioma, schwannoma, meningioma, adenocarcinoma, melanoma, and leukemia or lymphoid malignancies. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, small cell lung carcinoma, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulvar cancer, thyroid cancer, hepatic carcinoma, anal carcinoma, penile carcinoma, testicular cancer, esophageal cancer, tumors of the biliary tract, Ewing's tumor, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, testicular tumor, lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenstrom's macroglobulinemia, myelodysplastic disease, heavy chain disease, neuroendocrine tumors, schwannoma, and other carcinomas, as well as head and neck cancer.

Multi-Fc therapeutics may be used to treat autoimmune diseases. The term "autoimmune disease" as used herein refers to a varied group of more than 80 diseases and conditions. In all of these diseases and conditions, the underlying problem is that the body's immune system attacks the body itself. Autoimmune diseases affect all major body systems including connective tissue, nerves, muscles, the endocrine system, skin, blood, and the respiratory and gastrointestinal systems. Autoimmune diseases include, for example, systemic lupus erythematosus, rheumatoid arthritis, multiple sclerosis, myasthenia gravis, and type 1 diabetes.

The disease or condition treatable using the compositions and methods of the present invention may be a hematoimmunological process, including but not limited to sickle cell disease, idiopathic thrombocytopenic purpura, alloimmune/autoimmune thrombocytopenia, acquired immune thrombocytopenia, autoimmune neutropenia, autoimmune hemolytic anemia, parvovirus B19-associated red cell aplasia, acquired antifactor VIII autoimmunity, acquired von Willebrand disease, multiple myeloma and monoclonal gammopathy of unknown significance, sepsis, aplastic anemia, pure red cell aplasia, Diamond-Blackfan anemia, hemolytic disease of the newborn, immune-mediated neutropenia, refractoriness to platelet transfusion, neonatal, post-transfusion purpura, hemolytic uremic syndrome, systemic vasculitis, thrombotic thrombocytopenic purpura, or Evan's syndrome.

The disease or condition may also be a neuroimmunological process including, but not limited to, Guillain-Barre syndrome, chronic inflammatory demyelinating polyradiculoneuropathy, paraproteinemic IgM demyelinating polyneuropathy, Lambert-Eaton myasthenic syndrome, myasthenia gravis, multifocal motor neuropathy, lower motor neuron syndrome associated with anti-/GM1, demyelination, multiple sclerosis and optic neuritis, stiff man syndrome, paraneoplastic cerebellar degeneration with anti-Yo antibodies, paraneoplastic encephalomyelitis, sensory neuropathy with anti-Hu antibodies, epilepsy, encephalitis, myelitis, myelopathy especially associated with human T-cell lymphotropic virus-1, autoimmune diabetic neuropathy, Alzheimer's disease, Parkinson's disease, Huntington's disease, or acute idiopathic dysautonomic neuropathy.

The disease or condition may also be inflammation or autoimmunity associated with hearing loss or vision loss. For example, the disease or condition may be autoimmune-related hearing loss such as noise-induced hearing loss or age-related hearing loss, or may be associated with implantation of devices such as hearing devices (e.g., cochlear implants). In some embodiments, the compositions provided herein may be administered to a subject prior to, concurrently with, or subsequent to the implantation of a device.

The disease or condition may also be a rheumatic disease process including, but not limited to, Kawasaki's disease, rheumatoid arthritis, Felty's syndrome, ANCA-positive vasculitis, spontaneous polymyositis, dermatomyositis, antiphospholipid syndromes, recurrent spontaneous abortions, systemic lupus erythematosus, juvenile idiopathic arthritis, Raynaud's, CREST syndrome, or uveitis.

The disease or condition may also be a dermatoimmunological disease process including, but not limited to, toxic epidermal necrolysis, gangrene, granuloma, autoimmune skin blistering diseases including pemphigus vulgaris, bullous pemphigoid, pemphigus foliaceus, vitiligo, Streptococcal toxic shock syndrome, scleroderma, systemic sclerosis including diffuse and limited cutaneous systemic sclerosis, or atopic dermatitis (especially steroid dependent).

The disease or condition may also be a musculoskeletal immunological disease process including, but not limited to, inclusion body myositis, necrotizing fasciitis, inflammatory myopathies, myositis, anti-decorin (BJ antigen) myopathy, paraneoplastic necrotic myopathy, X-linked vacuolated myopathy, penacillamine-induced polymyositis, atherosclerosis, coronary artery disease, or cardiomyopathy.

The disease or condition may also be a gastrointestinal immunological disease process including, but not limited to, pernicious anemia, autoimmune chronic active hepatitis, primary biliary cirrhosis, celiac disease, dermatitis herpetiformis, cryptogenic cirrhosis, reactive arthritis, Crohn's disease, Whipple's disease, ulcerative colitis, or sclerosing cholangitis.

The disease or condition may also be graft versus host disease, antibody-mediated rejection of the graft, post-bone marrow transplant rejection, post-infectious disease inflammation, lymphoma, leukemia, neoplasia, asthma, type 1 diabetes mellitus with anti-beta cell antibodies, Sjogren's syndrome, mixed connective tissue disease, Addison's disease, Vogt-Koyanagi-Harada Syndrome, membranoproliferative glomerulonephritis, Goodpasture's syndrome, Graves' disease, Hashimoto's thyroiditis, Wegener's granulomatosis, micropolyarterits, Churg-Strauss syndrome, polyarteritis nodosa, or multisystem organ failure.

The disease or condition may be an antibody-mediated disease selected from the group consisting of Goodpasture's disease; solid organ transplantation rejection; neuromyelitis optica; neuromyotonia; limbic encephalitis; Morvan's fibrillary chorea syndrome; myasthenia gravis; Lambert Eaton myasthenic syndrome; autonomic neuropathy; Alzheimer's disease; atherosclerosis; Parkinson's Disease; stiff person syndrome or hyperekplexia; recurrent spontaneous abortion; Hughes syndrome; systemic lupus erythematosus; autoimmune cerebellar ataxia; connective tissue diseases including scleroderma, Sjogren's syndrome; polymyositis; rheumatoid arthritis; polyarteritis nodosa; CREST syndrome; endocarditis; Hashimoto's thyroiditis; mixed connective tissue disease; channelopathies; pediatric autoimmune neuropsychiatric disorders associated with Streptococcal infections (PANDAS); clinical conditions associated with antibodies against N-methyl-D-aspartate receptors especially NR1, contactin-associated protein 2, AMPAR, GluR1/GluR2, glutamic acid decarboxylase, GlyR alpha 1a, acetylcholine receptor, VGCC P/Q-type, VGKC, MuSK, GABA(B)R; aquaporin; and pemphigus. The disease or condition may be osteoarthritis.

The disease or condition may be a complement-mediated disease selected from the group consisting of myasthenia gravis, hemolytic uremic syndrome (HUS), atypical hemolytic uremic syndrome (aHUS), paroxysmal nocturnal hemoglobinuria (PNH), neuromyelitis optica, antibody-mediated rejection of allografts, nephropathy including membranous nephropathy, and nephritis including membranoproliferative glomerulonephritis (MPGN) and lupus nephritis.

The disease or condition may be a blood disorder including an anemia, such as sickle cell disease, including Hemoglobin SS, Hemoglobin SC, Hemoglobin S$\beta_0$ thalassemia, Hemoglobin S$\beta$+ thalassemia, Hemoglobin SD, and Hemoglobin SE.

The disease or condition may be an inflammatory disorder including age-related macular degeneration, Alzheimer's Disease, amyotrophic lateral sclerosis, or Parkinson's Disease.

"Allergy," as used herein, includes all immune reactions mediated by IgE as well as those reactions that mimic IgE-mediated reactions. Allergies are induced by allergens, including proteins, peptides, carbohydrates, and combinations thereof, that trigger an IgE or IgE-like immune response. Exemplary allergies include nut allergies, pollen allergies, and insect sting allergies. Exemplary allergens include urushiol in poison ivy and oak; house dust antigen; birch pollen components Bet v 1 and Bet v 2; the 15 kD antigen in celery; apple antigen Mal d 1; Pm p3 in peach; Timothy grass pollen allergen Phl p 1; Lol p 3, Lol p I, or Lol p V in Rye grass; Cyn d 1 in Bermuda grass; dust mite allergens dust mite Der p1, Der p2, or Der f1; α-gliadin and γ-gliadin epitopes in gluten; bee venom phospholipase A2; Ara h 1, Ara h 2, and Ara h 3 epitopes in peanuts.

The present invention further comprises methods for the treatment of diseases caused by infectious agents. Infectious agents include, but are not limited to, bacterial, mycological, parasitic, and viral agents. Examples of such infectious agents include the following: *Staphylococcus*, methicillin-resistant *Staphylococcus Aureus*, *Escherichia coli*, Streptococcaceae, Neisseriaaceae, cocci, Enterobacteriaceae, *Enterococcus*, vancomycin-resistant *Enterococcus*, *Cryptococcus*, *Histoplasma*, *Aspergillus*, Pseudomonadaceae, Vibrionaceae, *Campylobacter*, Pasteurellaceae, *Bordetella*, *Francisella*, *Brucella*, Legionellaceae, Bacteroidaceae, gram-negative bacilli, *Clostridium*, *Corynebacterium*, *Propionibacterium*, gram-positive bacilli, anthrax, *Actinomyces*, *Nocardia*, *Mycobacterium*, *Treponema*, *Borrelia*, *Leptospira*, *Mycoplasma*, *Ureaplasma*, *Rickettsia*, *Chlamydiae*, *Candida*, systemic mycoses, opportunistic mycoses, protozoa, nematodes, trematodes, cestodes, adenoviruses, herpesviruses (including, for example, herpes simplex virus and Epstein Barr virus, and herpes zoster virus), poxviruses, papovaviruses, hepatitis viruses, (including, for example, hepatitis B virus and hepatitis C virus), papilloma viruses, orthomyxoviruses (including, for example, influenza A, influenza B, and influenza C), paramyxoviruses, coronaviruses, picornaviruses, reoviruses, togaviruses, flaviviruses, bunyaviridae, rhabdoviruses, rotavirus, respiratory syncitial virus, human immunodeficiency virus and retroviruses. Exemplary infectious diseases include, but are not limited to, candidiasis, candidemia, aspergillosis, streptococcal pneumonia, streptococcal skin and oropharyngeal conditions, gram-negative sepsis, tuberculosis, mononucleosis, influenza, respiratory illness caused by respiratory syncytial virus, malaria, schistosomiasis, and trypanosomiasis.

All references cited herein are incorporated by reference in their entireties.

EXAMPLES

Example 1: GL-2045 Protected Antibody Opsonized Cells From CDC

Figure 1B:
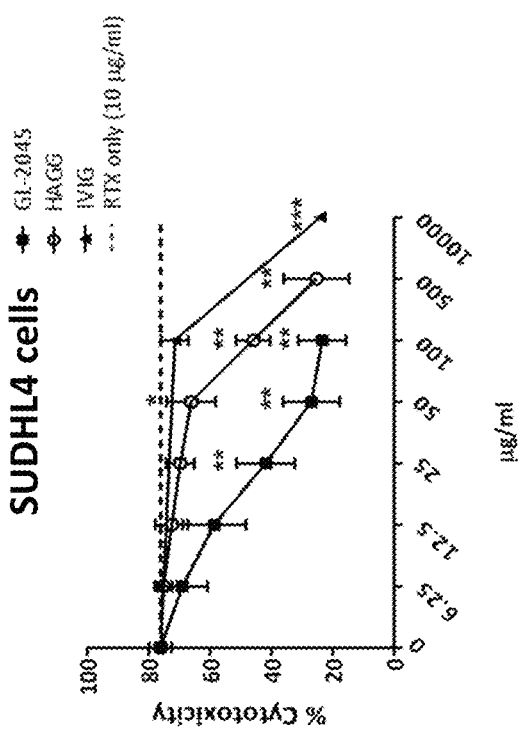

Experiments were performed to determine the therapeutically effective dose of GL-2045 for inhibition of complement-mediated cytotoxicity (CDC). Briefly, CD20+ B cell lymphoma lines, SUDHL4 and Ramos, were incubated with an anti-CD20 antibody (Rituximab, 10 µg/mL) on ice for 5 minutes in media with 2% FBS. Rituximab (RTX), GL-2045, heat-aggregated IVIG (HAGG), and IVIG (10, 50, 100, 500, 1000, and 10,000 µg/mL) were incubated with normal human serum for 10-15 minutes at 37° C. Sera/test compound mixtures were added to cells to a final concentration of 6%. Samples were incubated at 37° C. for 45 minutes. Cytotoxicity of SUDHL4 and Ramos cells was measured by flow cytometry detection of Annexin V/7-AAD staining. For both cell lines, the maximally effective dose of GL-2045 tested was 100 µg/mL. Further, GL-2045 was substantially more potent than IVIG at similar doses (FIG. 1A and FIG. 1B).

Example 2: GL-2045 Drove Limited Initial Complement Activation

Figure 2:
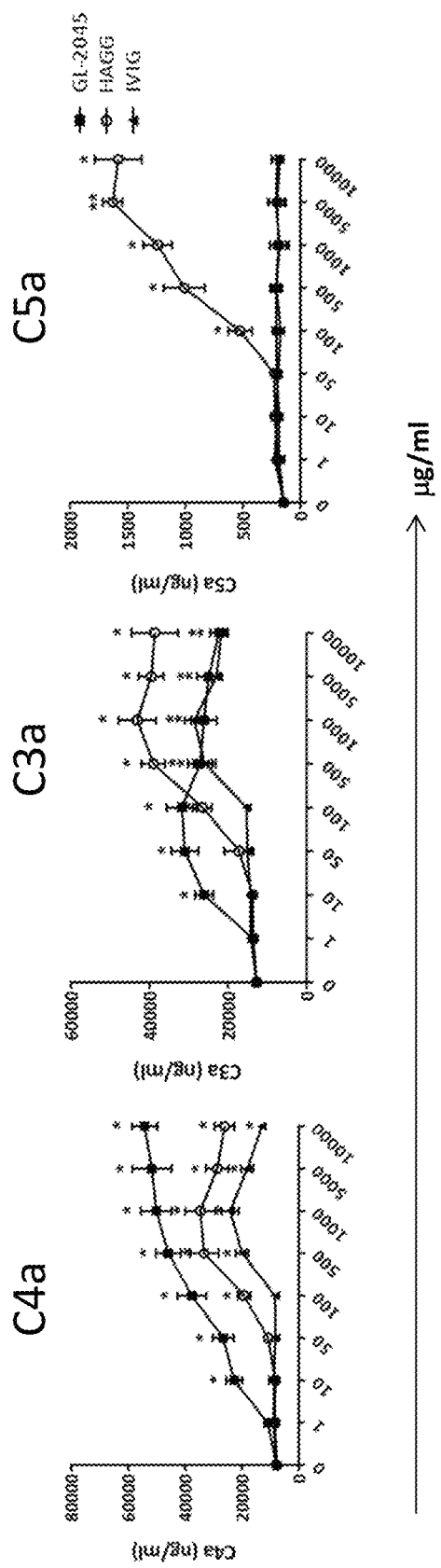
FIG. 2 illustrates concentrations of complement split products induced by GL-2045, HAGG, and IVIG in Factor H-sufficient serum

Experiments were performed to determine the mechanisms by which GL-2045 protected cells from CDC. In a cell free system, normal human serum (NETS) was incubated with increasing concentrations of GL-2045, HAGG, and IVIG (1-10,000 µg/mL) for 90 minutes at 37° C. Levels of complement split products C4a, C3a, and C5a were evaluated with the BD Biosciences CBA human anaphylatoxin kit (cat #561418). In this system, GL-2045 mediated significant cleavage of C4, indicated by an increase in C4a (FIG. 2, left panel), and modest cleavage of C3, indicated by a smaller increase in C3a (FIG. 2, middle panel). Further, serum treated with GL-2045 did not contain detectable levels of C5a (FIG. 2, right panel). These data demonstrate that GL-2045 activates the initial steps of classical complement activation, as demonstrated by C4a production, has a limited ability to mediate downstream C3 cleavage, and is unable to mediate C5 cleavage at the doses tested. The results indicated that GL-2045 drove limited initial complement activation with an inability to mediate downstream activation.

Example 3: Limited Complement Activation by GL-2045 was Dependent on Factor H

Figure 3:
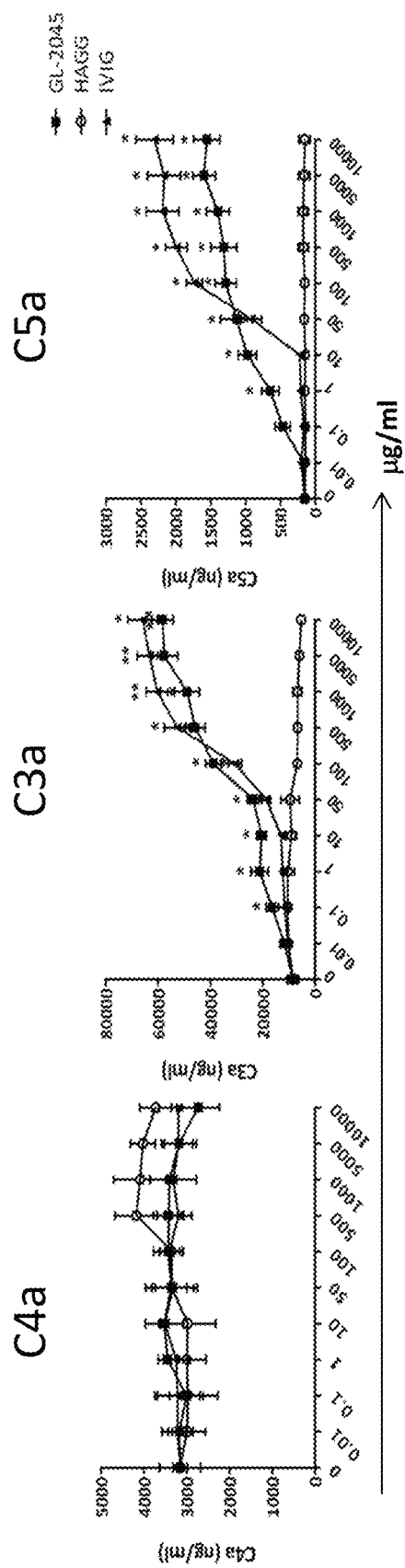
FIG. 3 illustrates concentrations of complement split products induced by GL-2045, HAGG, and IVIG in Factor H-deficient serum.
Figure 4:
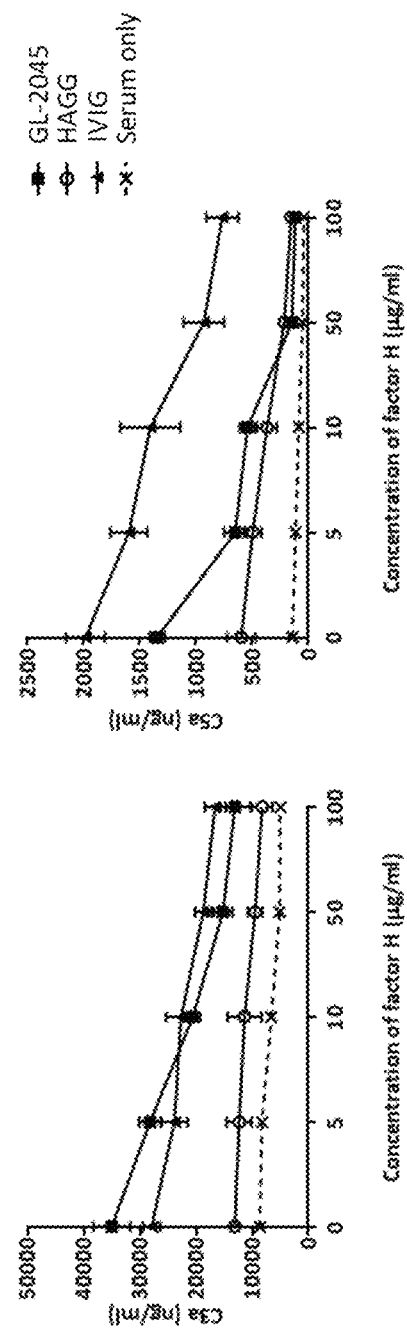
FIG. 4 illustrates the effects of GL-2045, HAGG, and IVIG on concentrations of C3a and C5a in Factor H-depleted serum that has been reconstituted with Factor H.

Based on the ability of GL-2045 to inhibit downstream complement activation, experiments were performed to determine whether or not regulators of complement activation, such as Factor H, were involved in the actions of GL-2045. Factor H is an important regulator of both alternative and classical complement activation, with an important role in preventing aberrant and excessive complement activation. Factor H-depleted serum was incubated with various concentrations of GL-2045, HAGG, and IVIG (0.01-10,000 µg/mL) and C4a, C3a, and C5a production were measured as indicators of upstream (C3a, C4a) and downstream (C5a) complement activation. In Factor H-depleted serum, no significant levels of C4a were observed for any of GL-2045, HAGG, or IVIG, indicating that Factor H may play a previously unreported role in initiating activation of the classical complement pathway (FIG. 3, left panel). Surprisingly, and in contrast to normal human serum, in Factor H depleted serum both GL-2045 and IVIG mediated the generation of significant levels of both C3a and C5a in the absence of Factor H (FIG. 3, middle and right panels). Reconstitution of Factor H-depleted serum with Factor H resulted in a concentration-dependent reduction in the levels of C3a and C5a following exposure to GL-2045 at 100 µg/mL and of IVIG at 100 µg/mL (FIG. 4). These data indicate that Factor H plays an important role in mediating the ability of multi-Fc therapeutics to inhibit downstream complement activation. In the presence of adequate Factor H, the absence of C5a generation upon exposure to multi-Fc therapeutics means that C3b is not incorporated into either the classical or the alternative C5 convertase but is instead degraded to iC3b.

Figure 5:
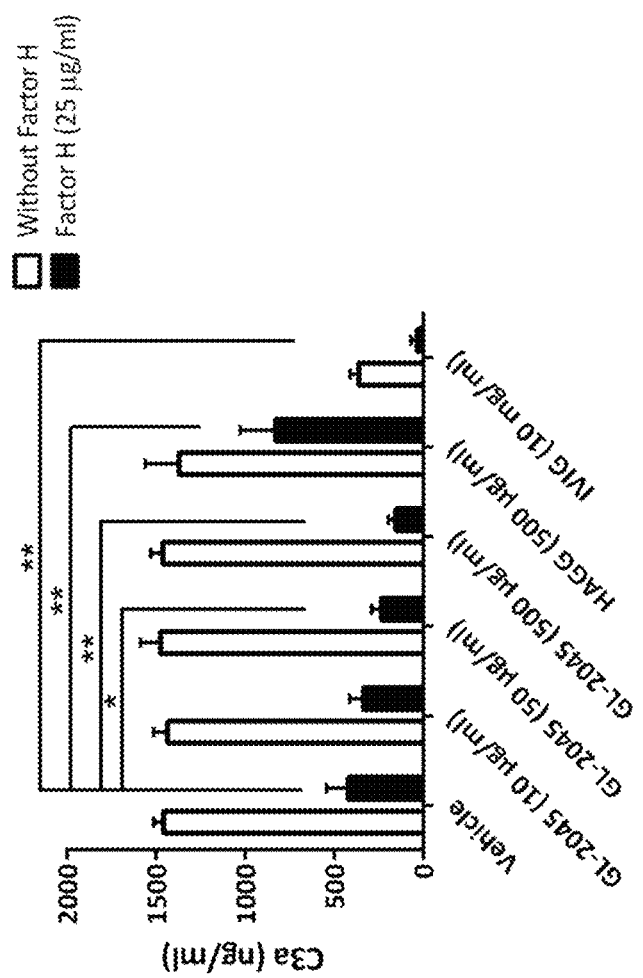
FIG. 5 illustrate the inhibitory activity of GL-2045 on the alternative form of C3 convertase in the presence of Factor H.
Figure 6A:
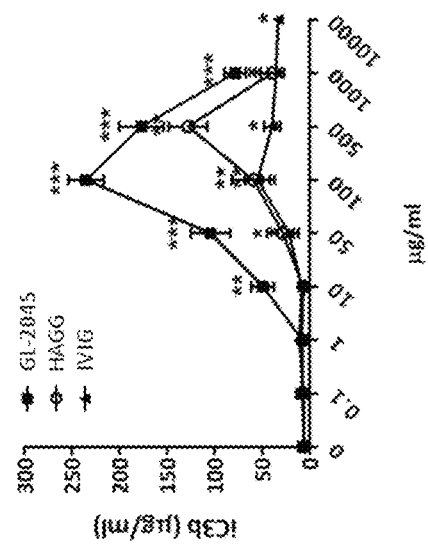
FIG. 6A-FIG. 6C illustrate the effects of GL-2045 on alternative C3 convertase activity in the presence of both Factor H and Factor I (FIG. 6A), and the effects of multi-Fc therapeutics on the production of iC3b (FIGS. 6B, 6C).

Example 4: GL-2045 Promoted the Function of Factor H and Factor I and Enhanced iC3b Generation Experiments were performed to determine to further define the interactions between GL-2045, Factor H, and Factor I. The alternative form of C3 convertase was generated by incubation of C3b, Factor D, Factor B, and C3 in the presence of GL-2045, HAGG, or IVIG, with (FIG. 5, black bars) or without Factor H (FIG. 5, white bars). As anticipated, Factor H inhibited the actions of alternative C3 convertase, indicated by a reduction in C3a. Surprisingly, addition of GL-2045 potentiated the inhibitory function of Factor H in a concentration-dependent manner, noted by a dose-dependent decrease in C3a (FIG. 5). As Factor H is a cofactor for Factor I, an analogous system was used to determine the interplay between Factor H, Factor I, and GL-2045. C3a generation was measured in the presence of a fixed, suboptimal concentration of Factor H (1 µg/mL) in the presence of increasing concentrations of Factor I (1 or 25 µg/mL). GL-2045 augmented the ability of Factors H and I to inhibit the alternative form of C3 convertase in a concentration-dependent manner (FIG. 6A, *p<0.05, **p<0.01). Thus, GL-2045 was able to inhibit downstream complement activation and to enhance the functions of Factor H and Factor I, even in the presence of suboptimal concentrations of Factor H.

Figure 6B:
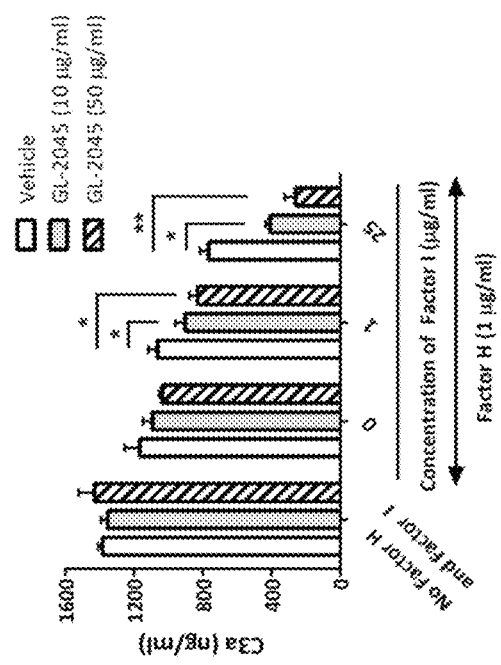
Figure 6C:
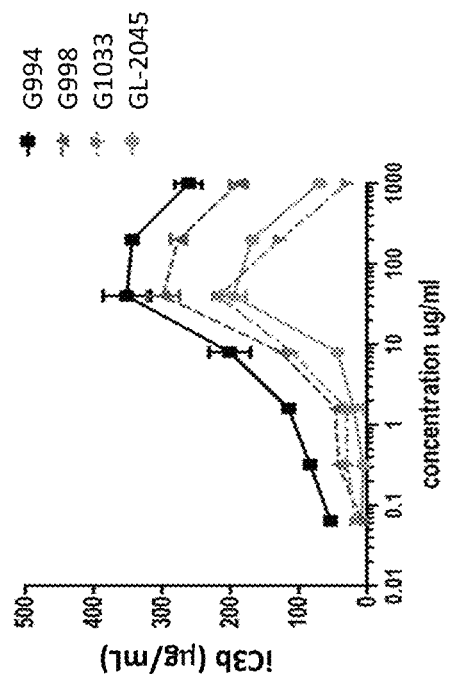

Further, the addition of the multi-Fc therapeutics GL-2045, G994, G998, and G1033 all induced significant levels of iC3b (FIGS. 6B and 6C). The levels of iC3b induced by the multi-Fc therapeutics demonstrated several important points. First, although GL-2045 and IVIG were able to induce increases in iC3b, GL-2045 induced higher overall levels of iC3b compared to IVIG (~250 µg/mL compared to ~40 µg/mL, respectively) suggesting that GL-2045 is more potent than IVIG in generating iC3b levels above a therapeutic threshold.

Second, in the absence of GL-2045, G994, G998, or G1033, there was no activation of the complement cascade and thus no iC3b generated as activation of the classical complement pathway is required for iC3b generation. In fact, concentrations of GL-2045, G994, G998, or G1003 at or below 1 µg/mL generated relatively little amounts of iC3b, while concentrations of the compounds between 10-100 µg/mL resulted in substantial iC3b generation. Third, the levels of iC3b peaked at 250 µg/mL in the presence of 100 µg/mL of GL-2045, and quickly tapered off with increasing concentrations of GL-2045 (FIG. 6B), indicating that there is a maximum drug effect and that further increases in the dose of the multi-Fc therapeutic drug may be detrimental. Surprisingly, 100 µg/mL of GL-2045 was also the maximally effective dose tested for inhibition of CDC (FIG. 1A and FIG. 1B). These data therefore indicate the potential for iC3b to serve as a proxy for the maximal therapeutically effective dose of GL-2045.

Example 5: iC3b Levels Correlate With Effective GL-2045 Dose In Vivo

Experiments are performed to assess the correlation of iC3b levels with GL-2045 therapeutic efficacy in murine models of nephritis. In this model, an antibody to thymocytes (ATS) that is reactive to surface Thy-1 antigen present on rat mesangial cells is used (Yamamoto 1987 and Jefferson 1999). Administration of ATS induces a complement-dependent mesangiolysis followed by a rapid mesangial proliferative glomerulonephritis that peaks within 5 days after injection, and then resolves over time.

Disease was induced at day 0 by injection of mouse anti-rat CD90 (Thy1.1) (Cedar Lane) in Wistar rats (n=8) to induce glomerulonephritis. On days 0, 2, 4, and 6, animals were treated with different doses of CDC inhibitory stradomers. Control, non-diseased animals did not receive anti-Thy 1 antibody or other treatment. Positive control Tacrolimus is dosed at 1 mg/kg intramuscular dosed daily starting at day −9 before antisera injection. Day 0 dosing was 4 hours before antisera injection. Urine was collected before dosing and at day 3, 5, 7 and 9 following antisera injection. Kidneys are collected from rats at end of study and fixed in 10% formalin for histology analysis. Serum is collected for serum BUN analysis and determination of iC3b levels.

Figure 7A:
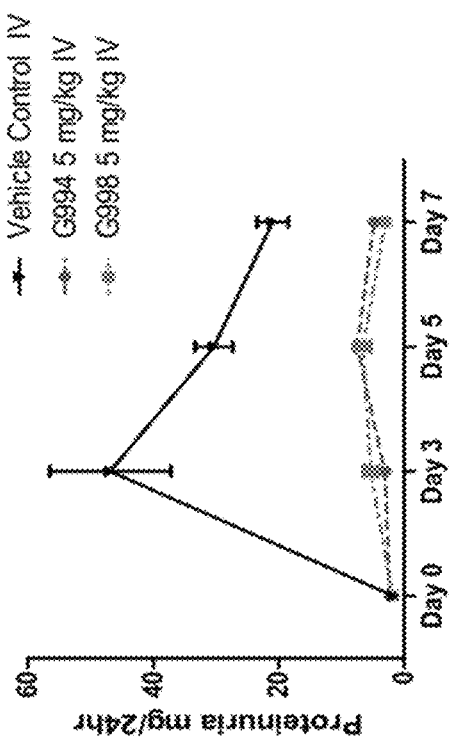
FIG. 7A-FIG. 7B illustrate the effects of G998 on proteinuria in a Thy-1 model of nephritis.
Figure 7B:
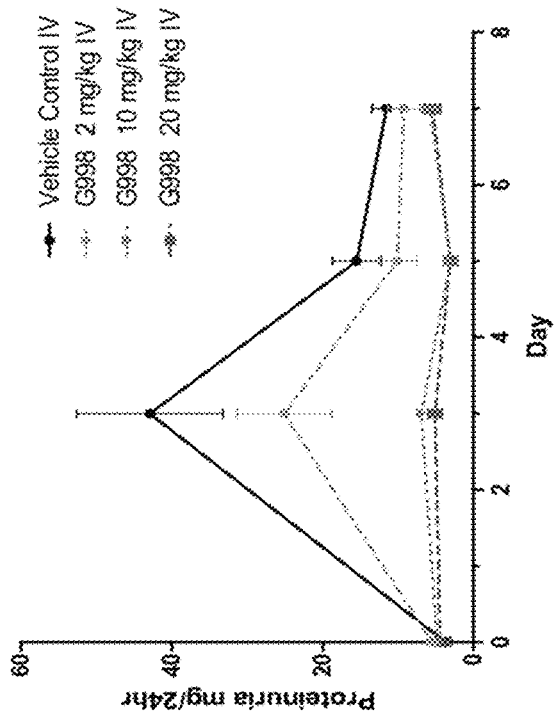

FIG. 7A-7B illustrate the effects of G998 at different doses on protection from proteinuria (FIG. 7A) and the effects of G994 and G998 on protection from proteinuria (FIG. 7B) in the Thy-1 model of nephritis. FIG. 7A demonstrates partial efficacy of G998 at 2 mg/Kg IV in this model and complete efficacy at doses of 10 mg/Kg IV and above. Additional results will demonstrate that differing doses of the multi-Fc therapeutic G998 are associated with differing levels of iC3b generation, C3a generation, and C4a generation. Additional results will also demonstrate that the dose corresponding to the maximal therapeutic effect of a multi-Fc therapeutic also generates the maximal increase over baseline in iC3b. Additionally, the inventors have found that current rat ELISA kits specific for C3a unintentionally also pick up C3, i.e. are not specific for C3a+C3a desArg. FIG. 7B demonstrates that both G994 and G998 dosed at 5 mg/Kg IV were associated with complete efficacy in this model. Further results will demonstrate that the therapeutically effective dose of G994 and G998 (e.g., the dose at which protection from proteinuria generation, diminished histological evidence of nephritis, and/or decreased BUN levels compared to placebo treatment) correlates with exceeding threshold levels of iC3b detected in serum.

The invention claimed is:

1. A method for determining an effective dose of a multi-Fc therapeutic comprising:
   (a) administering the multi-Fc therapeutic to a subject in need thereof at a starting dose of the multi-Fc therapeutic;
   (b) determining blood iC3b level of the subject;
   (c) determining that the subject requires a first cumulative escalated dose of the multi-Fc therapeutic if the subject has been determined to have:
      (i) a blood iC3b level lower than a predetermined threshold following administration with the starting dose of the multi-Fc therapeutic; or
      (ii) a blood iC3b level with a change percent of less than 10%, less than 20%, less than 30%, less than 40%, or less than 50% from baseline; and
   (d) administering a first cumulative escalated dose of the multi-Fc therapeutic, wherein the multi-Fc therapeutic comprises multimers of a homodimer and wherein the homodimer comprises a monomer comprising amino acids 21-264 of SEQ ID NO:4.

2. The method of claim 1, further comprising:
   (e) repeating the determination of the blood iC3b level of the subject after administration of the first cumulative escalated dose of the multi-Fc therapeutic; and
   (f) administering a second cumulative escalated dose of the multi-Fc therapeutic that is higher than the first cumulative escalated dose if the subject is determined to have:
      (i) a blood iC3b level lower than a predetermined threshold following administration with the starting dose of the multi-Fc therapeutic; or
      (ii) a blood iC3b level with a change percent of less than 10%, less than 20%, less than 30%, less than 40%, or less than 50% from baseline.

3. The method of claim 1, wherein the determination of blood iC3b level is repeated with continued cumulative escalated doses of the multi-Fc therapeutic until the predetermined threshold of blood iC3b level is met, or until the blood iC3b level has changed by greater than 10%.

4. The method of claim 1, wherein the first cumulative escalated dose of the multi-Fc therapeutic is at least 105% of the starting dose of said multi-Fc therapeutic.

5. The method of claim 1, wherein administering a cumulative escalated dose comprises administering an escalated dose of the multi-Fc therapeutic throughout the dosing period.

6. The method of claim 1, wherein administering a cumulative escalated dose comprises administering both an escalated dose and an incremental dose during the dosing period.

7. The method of claim 1, wherein the cumulative escalated dose of the multi-Fc therapeutic is at least 110%, 115%, 120%, 125%, 150%, 175%, or 200% of the previously administered dose of said multi-Fc therapeutic.

8. The method of claim 1, wherein the predetermined threshold of blood iC3b level is 25 µg/mL to 300 µg/mL, 50 µg/mL to 200 µg/mL, 75 µg/mL to 125 µg/mL, or 100 µg/mL.

9. The method of claim 1, wherein the predetermined threshold of blood iC3b level is 25% of neutrophils and monocytes that are iC3b+.

10. The method of claim 1, wherein the predetermined threshold of blood iC3b level is an iC3b mean fluorescence intensity (MFI) of 125% of the baseline iC3b MFI.

11. The method of claim 1, wherein the percent change is less than 10%.

12. The method of claim 1, wherein the blood iC3b level is determined by measurement of a surrogate marker for iC3b.

13. The method of claim 12, wherein the surrogate marker for iC3b is selected from the group consisting of iC3b1, iC3b2, C3a, C3a desArg, C4a, C4a desArg, C3f, C3dg, C3d, C3g and a combination thereof.

14. The method of claim 12, wherein the surrogate marker for iC3b is C3a or C4a.

15. The method of claim 12, wherein the predetermined threshold for the surrogate marker of iC3b is less than 30 ng/ml, less than 20 ng/ml, less than 10 ng/mL or less than 5 ng/mL.

16. The method of claim 12, wherein the percent change of the surrogate marker is less than 10%, less than 20%, less than 30%, less than 40%, or less than 50%.

17. The method of claim 1, wherein the subject has an autoimmune or inflammatory disease, wherein the autoimmune or inflammatory disease is selected from the group consisting of autoimmune cytopenia, idiopathic thrombocytopeniarpura (ITP), rheumatoid arthritis, systemic lupus erythematosus, asthma, Kawasaki disease, Guillain-Barre syndrome, Stevens-Johnson syndrome, Crohn's colitis, diabetes, chronic inflammatory demyelinating polyneuropathy (CIDP), myasthenia gravis, anti-Factor VIII autoimmune disease, dermatomyositis, vasculitis, uveitis, and Alzheimer's disease.

18. The method of claim 1, wherein the blood iC3b level is determined by an immunoassay.

19. The method of claim 18, wherein the immunoassay comprises an ELISA or a western blot.

20. The method of claim 1, wherein the blood iC3b level is determined by flow cytometry.

* * * * *

SEQUENCE LISTING

```
<160> NUMBER OF SEQ ID NOS: 5

<210> SEQ ID NO 1
<211> LENGTH: 12
<212> TYPE: PRT
<213> ORGANISM: Homo sapiens

<400> SEQUENCE: 1

Glu Arg Lys Cys Cys Val Glu Cys Pro Pro Cys Pro
1               5                   10

<210> SEQ ID NO 2
<211> LENGTH: 232
<212> TYPE: PRT
<213> ORGANISM: Homo sapiens

<400> SEQUENCE: 2

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 3
<211> LENGTH: 232
```

```
<212> TYPE: PRT
<213> ORGANISM: Homo sapiens

<400> SEQUENCE: 3

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230

<210> SEQ ID NO 4
<211> LENGTH: 264
<212> TYPE: PRT
<213> ORGANISM: Homo sapiens

<400> SEQUENCE: 4

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110
```

```
Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
                260

<210> SEQ ID NO 5
<211> LENGTH: 264
<212> TYPE: PRT
<213> ORGANISM: Homo sapiens

<400> SEQUENCE: 5

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Asp Glu Leu Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220
```

```
Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260
```